(12) United States Patent
Stollery et al.

(10) Patent No.: US 9,090,427 B2
(45) Date of Patent: Jul. 28, 2015

(54) LIFTING DEVICE AND METHOD FOR GLOVES STACKING

(75) Inventors: Jonathan William Stollery, Woodbridge (GB); Kim Marie Stollery, Woodbridge (GB)

(73) Assignee: Altevo Limited, Woodbridge, Suffolk (GB)

( * ) Notice: Subject to any disclaimer, the term of this patent is extended or adjusted under 35 U.S.C. 154(b) by 214 days.

(21) Appl. No.: 13/503,080

(22) PCT Filed: Oct. 20, 2010

(86) PCT No.: PCT/GB2010/051765
§ 371 (c)(1),
(2), (4) Date: Apr. 20, 2012

(87) PCT Pub. No.: WO2011/048414
PCT Pub. Date: Apr. 28, 2011

(65) Prior Publication Data
US 2012/0207577 A1    Aug. 16, 2012

(30) Foreign Application Priority Data

Oct. 20, 2009   (GB) .................................. 0918345.0
Apr. 13, 2010   (GB) .................................. 1006114.1

(51) Int. Cl.
*B65H 29/32* (2006.01)
*B65H 29/24* (2006.01)
(Continued)

(52) U.S. Cl.
CPC ................. *B65H 29/24* (2013.01); *B65B 35/50* (2013.01); *B65B 35/58* (2013.01); *B65B 57/10* (2013.01);
(Continued)

(58) Field of Classification Search
CPC ........ B65H 29/24; B65H 29/32; B65B 35/58; B65B 63/045; B65B 57/10; B65B 35/50

USPC ............. 414/793, 793.2, 793.4, 793.8, 788.4, 414/788.1, 792.8, 794.2, 794.4; 493/405; 53/447, 540, 446, 544

See application file for complete search history.

(56) References Cited

U.S. PATENT DOCUMENTS

| 797,753 A | 8/1905 | Roth |
| 797,754 A | 8/1905 | Roth |

(Continued)

FOREIGN PATENT DOCUMENTS

| DE | 1299515 | 7/1969 |
| DE | 19756032 | 6/1999 |

(Continued)

OTHER PUBLICATIONS

International Search Report in PCT application PCT/GB2010/051765, Mar. 9, 2011, EPO.

(Continued)

*Primary Examiner* — Saul Rodriguez
*Assistant Examiner* — Lynn Schwenning

(57) ABSTRACT

A glove stacking apparatus and a method of stacking gloves for preparing a stack of gloves prior to packing into a box. A glove stacking apparatus comprises a lifting means for lifting each of the gloves. The lifting means includes an attractive glove lifting surface including a movable member being movable from a first position in which the movable member is substantially flush with the lifting surface to a second position in order to help dislodge the lifted glove from the lifting surface. The movable member has a surface that is permeable to air flow through the surface, while the glove lifting means including a source of positive air pressure and means to control the application of said positive air pressure through the permeable surface of the movable member in order to control the dislodging of the lifted glove from the glove lifting surface.

15 Claims, 15 Drawing Sheets

(51) Int. Cl.
  *B65B 35/58*   (2006.01)
  *B65B 63/04*   (2006.01)
  *B65B 57/10*   (2006.01)
  *B65B 35/50*   (2006.01)
  *B65B 5/06*    (2006.01)
  *B65B 25/20*   (2006.01)

(52) U.S. Cl.
  CPC ............... *B65B 63/045* (2013.01); *B65B 5/06* (2013.01); *B65B 25/20* (2013.01); *B65H 2301/332* (2013.01); *B65H 2301/4472* (2013.01); *B65H 2301/44734* (2013.01); *B65H 2406/12* (2013.01); *B65H 2406/351* (2013.01); *B65H 2511/216* (2013.01); *B65H 2555/31* (2013.01)

(56) References Cited

U.S. PATENT DOCUMENTS

| | | | |
|---|---|---|---|
| 1,855,846 A * | 4/1932 | Shimer | 53/399 |
| 2,629,519 A * | 2/1953 | Neckel | 223/37 |
| 2,638,256 A | 5/1953 | Hagen et al. | |
| 2,665,039 A * | 1/1954 | Neckel | 223/37 |
| 3,072,314 A | 1/1963 | Keene | |
| 3,167,223 A | 1/1965 | Weiss | |
| 3,406,966 A * | 10/1968 | Walton | 271/176 |
| 3,490,764 A | 1/1970 | Muller et al. | |
| 3,601,396 A | 8/1971 | Rovin | |
| 3,886,712 A * | 6/1975 | Sylvester | 53/429 |
| 4,008,887 A * | 2/1977 | Karolyi | 493/457 |
| 4,433,599 A | 2/1984 | Mundus et al. | |
| 4,805,374 A * | 2/1989 | Yawberg | 53/120 |
| 4,874,158 A | 10/1989 | Retzloff | |
| 5,542,566 A | 8/1996 | Glaug et al. | |
| 5,642,601 A * | 7/1997 | Thompson et al. | 53/431 |
| 5,697,762 A * | 12/1997 | Thompson et al. | 414/792.9 |
| 5,810,349 A * | 9/1998 | Bloser et al. | 271/213 |
| 5,816,440 A * | 10/1998 | Shields et al. | 221/45 |
| 6,336,492 B1 | 1/2002 | Nagaoka | |
| 6,901,723 B2 * | 6/2005 | Jordan et al. | 53/429 |
| 7,052,009 B2 * | 5/2006 | Roth | 271/182 |
| 2003/0017929 A1 * | 1/2003 | Engesser | 493/162 |
| 2004/0042789 A1 | 3/2004 | Puffer, Jr. et al. | |
| 2005/0175439 A1 * | 8/2005 | Engesser | 414/788.1 |
| 2006/0218700 A1 * | 10/2006 | Uda | 2/400 |
| 2006/0283151 A1 * | 12/2006 | Welborn et al. | 53/475 |
| 2011/0062179 A1 * | 3/2011 | Stollery et al. | 221/45 |
| 2011/0162325 A1 * | 7/2011 | Stollery et al. | 53/447 |
| 2012/0204517 A1 * | 8/2012 | Stollery et al. | 53/447 |

FOREIGN PATENT DOCUMENTS

| | | |
|---|---|---|
| DE | 29916095 | 9/1999 |
| DE | 29916095 | 2/2000 |
| EP | 0348311 | 12/1989 |
| EP | 0796791 | 9/1997 |
| EP | 1568448 | 8/2005 |
| FR | 2290282 | 6/1976 |
| FR | 2499042 | 11/1980 |
| FR | 2558442 | 1/1984 |
| GB | 1344376 | 1/1974 |
| GB | 1455147 | 11/1976 |
| GB | 2242107 | 9/1991 |
| GB | 2245879 | 1/1992 |
| GB | 2474726 | 4/2011 |
| JP | 04239405 | 8/1992 |
| JP | 6039768 | 2/1994 |
| JP | 09142406 | 6/1997 |
| JP | 10180670 | 7/1998 |
| WO | WO 2010020782 | 2/2010 |

OTHER PUBLICATIONS

Written Opinion for PCT application PCT/GB2010/051765, Mar. 17, 2011, EPO.
Search Report in European Application GB1006114.1, Aug. 6, 2010, United Kingdom Intellectual Property Office.

* cited by examiner

LIFTING DEVICE AND METHOD FOR GLOVES STACKING

BACKGROUND a. Field of the Invention

The present invention relates to a glove stacking apparatus for preparing a stack of gloves prior to packing into a box, and to a method of stacking gloves using a glove stacking apparatus for preparing a stack of gloves prior to packing into a box, particularly ambidextrous disposable hygienic gloves.

b. Related Art

The control of infection of patients in hospitals, clinics, and doctors' surgeries has become an ever more pressing concern with the rise of infectious bacteria resistant to multiple antibiotics, in particular methicillin-resistant *staphylococcus aureus* (MRSA) and *Clostridium difficile* (*C. difficile*). In the United Kingdom alone there are thought to be about 5,000 deaths a year from infections caught in hospitals but some experts believe the number could be as high as 20,000.

Disposable medical gloves can help prevent cross-contamination, but a problem arises if external parts of the glove touch the same areas of a dispensing container as have previously been touched by hands which are contaminated with harmful micro-organisms. Such external parts of the gloves can then become contaminated prior to contact with a patient, if these external parts are the fingers or palm area of the glove the likelihood of a patient being contaminated is dramatically increased.

Most gloves used in hospitals and clinics are examination gloves, and these are used in large numbers. Such gloves are supplied not in individual sterile packages, but in relatively inexpensive cardboard dispensing boxes. The size of boxed gloves is an issue owing to the need to minimize the space needed to store gloves, or the size of dispensing apparatus holding boxed gloves.

Because of the need to enhance infection control, the preferred method of dispensing these gloves is by the cuff, so that the user can only remove the gloves from the container by the cuffs rather than by the glove fingers. Examples of cuff first glove dispensing systems are disclosed in GB 2449087, GB 2457450 and GB 2454753. Gloves are packed in an inexpensive box, made from card material and having a removable cover over an opening, with each glove either packed flat or folded over on itself and with the cuff of each glove being presented towards the opening.

Although such cuff first glove dispensing systems are helpful in controlling contamination of the finger portions of each glove during dispensing and donning of each glove, a problem arises in how to pack the maximum number of gloves in each box for increased economy. Although it is possible to arrange gloves into a stack by hand, this is time consuming and relatively expensive in a production environment.

It is an object of the present invention to provide an apparatus and method for stacking gloves prior to packing in a dispensing box. It is also an object of the present invention to reduce the packing volume of boxed gloves.

SUMMARY OF THE INVENTION

According to the invention, there is provided a glove stacking apparatus for forming a stack of gloves comprising:
a packing recess for receiving said gloves to be stacked and for containing said stack as the stack is being formed, said recess having a pair of opposite side edges and having a movable floor within said recess which, in use, is lowered as the stack of gloves grows whereby said stack of gloves continues to be retained within said recess as gloves are added to the stack; and
a glove placement means for moving and depositing said gloves at said recess one of top of another for forming said stack of gloves;
wherein the glove placement means is arranged to deposit said gloves with a portion of said gloves overlapping alternately one or the other of said opposite side edges of said recess as subsequent gloves are deposited and the apparatus comprises a pair of movable flaps adjacent said opposite side edges of said recess for folding alternately inwards toward said recess said portions of said gloves overlapping alternately one or another of said opposite side edges of said recess.

Also described herein is a glove stacking apparatus for lifting and depositing gloves to be stacked, comprising a lifting means for lifting each of said gloves, said lifting means including an attractive glove lifting surface, wherein the lifting means includes within the lifting surface a movable member, the movable member being movable from a first position in which the movable member is substantially flush with the lifting surface to a second position in which the movable member stands proud of the lifting surface in order to help dislodge said lifted glove from the lifting surface, and the movable member has a surface that is permeable to air flow through said surface, the glove lifting means including a source of positive air pressure and means to control the application of said positive air pressure through said permeable surface of the movable member in order to control the dislodging of said lifted glove from the glove lifting surface.

Also according to the invention there is provided a method of stacking gloves using a glove stacking apparatus, said apparatus comprising a packing recess for receiving said gloves to be stacked, a glove placement means, a movable floor within said recess and a pair of movable flaps adjacent a pair of opposite side edges of said recess, the method comprising the steps of:
using the glove placement means to deposit gloves at said recess for stacking;
lowering the floor as required as the stack of gloves grows within said recess whereby said stack of gloves continues to be retained within said recess as gloves are added to the stack;
using the glove placement means to deposit said gloves such that at least one portion of each of said gloves overlaps alternately one or the other of said opposite side edges of said recess;
alternately using one or the other of said movable flaps to fold towards said recess said at least one portion of said glove overlapping said edge; and
repeating the preceding steps to form a stack of gloves within the bounds of the said recess.

Also described herein is a method of lifting and depositing gloves to be stacked using a glove stacking apparatus including an attractive glove lifting surface with a glove lifting portion, and a movable member within the lifting surface, the movable member having a surface that is permeable to air flow through said surface, the method comprising the steps of:
moving the lifting surface so that the lifting surface is above a glove to be lifted;
with the movable member in a first position in which the movable member is substantially flush with the lifting surface, using the attractive glove lifting surface to pull said glove to the lifting portion;
moving the lifting surface to a location where gloves are to be stacked;

releasing the glove from the attractive glove lifting surface;

moving the movable member to a second position in which the movable member stands proud of the lifting surface in order to help dislodge said lifted glove from the lifting surface;

applying a positive air pressure through said permeable surface of the movable member in order to control the dislodging of said lifted glove from the glove lifting surface; and depositing said dislodged glove at said location and repeating the preceding steps to form said stack of gloves.

The attractive lifting surface and movable member may be part of a glove placement means, for example including also actuators for controlling the movement of the lifting surface.

The glove lifting surface may have a permeable glove lifting portion. With the movable member in a first position in which the movable member is substantially flush with the lifting surface, a vacuum pressure is then applied through the permeable glove lifting portion to pull said glove to the lifting portion. The lifting surface is then moved to a location where gloves are to be stacked, following which the glove is released from the attractive glove lifting surface by releasing the vacuum pressure.

The movable member may, for example, be a downwardly acting piston. The movable member is preferably moved to said second position after said positive air pressure is applied through said permeable surface of the movable member. The application of the positive air pressure through the permeable surface of the movable member serves, in use, to press a portion of the deposited glove against the glove stack prior to compression of the stack by the movable member.

Also described herein is a glove stacking apparatus for forming a stack of gloves, comprising:

a glove placement means for depositing gloves one of top of another for forming said stack of gloves, the glove placement means including a lifting surface with a attractive glove lifting portion and a movable member within the lifting surface, the movable member being movable from a first position in which the movable member is substantially flush with the lifting surface to a second position in which the movable member stands proud of the lifting surface in order to help dislodge said lifted glove from the lifting surface;

a packing recess for receiving said gloves and for containing said stack as the stack is being formed, the packing recess having a downwardly movable floor; and means for moving the floor downwardly so that the stack of gloves continues to be retained within the recess as gloves are added to the stack;

wherein the movable member is arranged, in use, to compress the stack of gloves within the recess after each glove is deposited.

Preferably, the compression of the stack of gloves by the movable member provides a motive force for the means for moving the floor downwardly.

The means for moving the floor downwardly may, in use, be activated to move downwards by pressure from the movable member compressing the stack of gloves.

The means for moving the floor downwardly may comprise an upwardly acting spring mechanism, the floor being supported by this spring mechanism. The spring mechanism may provide an upwards restoring force against the compression of the stack of gloves by the movable member. The spring mechanism may also be compressible to lower the level of the floor when the stack of gloves is compressed by the movable member, this compression of the spring mechanism serving, in use, to limit a compression force on the stack of glove by the movable member.

Also described herein is a method of forming a stack of gloves using a glove stacking apparatus comprising a glove placement means having an attractive lifting surface, a movable member within the lifting surface, the movable member being movable from a first position in which the movable member is substantially flush with the lifting surface to a second position in which the movable member stands proud of the lifting surface and a packing recess, said recess having a downwardly movable floor, the method comprising the steps of:

using the attractive lifting surface of the glove placement means to lift and deposit gloves one on top of another to form said stack of gloves within the recess;

prior to depositing said gloves moving the movable member from said first position to said second position in order to help dislodge said gloves from said attractive lifting surface;

moving the floor downwardly as the stack of gloves is formed in order to retain the stack of gloves within the recess as gloves are added to the stack; and using the movable member to compress air out of the stack of gloves after depositing each glove on said stack.

The glove placement means may be used in an apparatus for stacking gloves in a stack which comprises at least one conveyor for transporting said gloves to be stacked, a sensing means for sensing the presence of said transported gloves on said conveyor, a processing means, a stacking station and a glove placement means for moving said transported gloves from said glove conveyor to form said stack at the stacking station, wherein:

the glove placement means includes a lifting and depositing portion for lifting each of said gloves to be moved from said conveyor and for depositing each of said lifting gloves at the stacking station; and the processing means is connected to the sensing means and to the glove placement means for controlling the operation of the glove placement means in accordance with said sensed presence so that, in use, the lifting and depositing portion of the glove placement means lifts gloves from said conveyor and deposits said gloves to form said stack.

The sensing means may sense additionally the orientation of a cuff portion and/or thumb portion of each of the transported gloves on the conveyor, and the processing means may be arranged to control the operation of the glove placement means in accordance with the sensed orientation so that, in use, the lifting and depositing portion of the glove placement means lifts gloves from the conveyor and deposits the gloves to form the stack with the cuff portion and/or the thumb portion of each glove in a desired orientation with respect to other gloves in the stack.

The apparatus may comprise additionally a pneumatic system, the pneumatic system being arranged to apply a vacuum to the lifted glove in order to adhere the lifted glove to the lifting portion.

Preferably, the apparatus comprises means to de-adhere the lifted glove for depositing at the stacking station.

For example, the pneumatic system may be arranged to apply a positive air pressure to the lifted glove in order to de-adhere the lifted glove for depositing at the stacking station.

The processing means may be connected to the pneumatic system for controlling the operation of the pneumatic system during the lifting and depositing of the gloves.

The packing station may comprise a recess in a work surface for containing the stack of gloves as gloves are deposited at the packing station.

Preferably, the lifting and depositing portion includes a lifting surface against which in use the gloves are held when moved and positioned by the apparatus prior to depositing for stacking.

The lifting and depositing means may include within the lifting surface a movable member, for example a downwardly acting piston. The movable member may be movable from a first position in which the movable member is substantially flush with the lifting surface to a second position in which the movable member stands proud of the lifting surface in order to help dislodge the lifted glove from the lifting surface prior to depositing for stacking.

The glove placement means may be used in a method of stacking gloves in a stack using a glove stacking apparatus that comprises at least one conveyor, a sensing means, a processing means, a stacking station, a glove placement means, the method comprising the steps of:
  using said conveyor to transport said gloves to be stacked;
  using said sensing means to sense the presence of said transported gloves on said conveyor;
  using the glove placement means to move said transported gloves from said glove conveyor to form said stack at the stacking station;
  wherein the processing means is connected to the sensing means and to the glove placement means for controlling the operation of the glove placement means in accordance with said sensed presence so that the glove placement means lifts gloves from said glove conveyor and deposits said gloves to form said stack.

When the glove placement means includes a lifting and depositing portion, this may be used to lift each of the gloves to be moved from the conveyor and to deposit each of the lifted gloves at the stacking station.

The glove placement means may also be used in an apparatus for stacking ambidextrous gloves in a stack with the thumbs of each glove in a desired orientation with respect to each other, at least two glove conveyors for transporting said gloves to be stacked, a glove transfer means, and a glove placement means for moving said transported gloves from said glove conveyors to form said stack, wherein:
  said conveyors includes a first conveying means and a second conveying means, the first conveying means leading to the second conveying means and the glove transfer means being operable to transfer said transported gloves from the first conveying means to the second conveying means;
  each glove has either a left handed orientation or a right handed orientation from the perspective of the glove placement means when removing said gloves from said conveyors;
  the second conveying means is arranged to convey said transferred gloves such that the handedness of each of said gloves transferred to the second conveying means is reversed from a left handed orientation to a right handed orientation or alternatively from a right handed orientation to a left handed orientation as the second conveying means transports said gloves; and
  the glove placement means is operable to move gloves from either of the first or second conveying means depending on a desired handedness of the next glove to be stacked.

There may be at least two conveyors which are part of a glove transport means for transporting gloves to be stacked and apparatus comprises additionally a sensing means for sensing the orientation of transported gloves, and also a processing means. The sensing means is arranged to sense the orientation of the transported gloves prior to the transfer means. The processing means is connected to the sensing means and is arranged to determine from the sensed orientation the handedness of the transported gloves, this handedness being either a left handed orientation of the glove thumb or alternatively a right handed orientation the glove thumb from the perspective of the sensing means. The processing means is then operable to determine the desired handedness of each of said gloves to be moved by the glove transport means and is connected to the glove transfer means, and is operable to use the glove transfer means to transfer the transported gloves from the first conveying means to the second conveying means to reverse the handedness of a glove when the sensed handedness is not the desired handedness. The glove placement means is operable to move gloves from the second conveying means when the sensed handedness is not the desired handedness or alternatively to move gloves from another one of the conveying means when the sensed handedness is the desired handedness.

Preferably, the gloves are transported and manipulated individually by the glove placement means.

The first conveying means is preferably a single continuous conveyor. It would, however, be possible to form the first conveying means from a series of consecutive conveyors, one passing gloves to the next conveyor in the series.

The first conveying means is preferably arranged to transport the gloves in a first direction of travel towards the glove transfer means and the second conveying means is preferably arranged to rotate the orientation of the transferred gloves about an axis transverse to the first direction so that said rotated transferred gloves travel in a second direction opposite the first direction.

The second conveying means may be a belt conveyor arranged in a loop. The second conveying means is arranged to convey the transferred gloves around at least a portion of the loop in order to change the handedness of each of said transferred gloves.

The rotation of the glove is then effected by the movement of the transferred glove from one side of the loop to an opposite side of the loop.

The first conveying means may be arranged to transport gloves along a first direction of travel towards a transfer portion of the first conveying means, this transfer portion being proximate the second conveying means.

The sensing means may be arranged to sense the orientation of each glove with respect to a first direction of travel as transported by the first conveying means.

The first conveying means and second conveying means are preferably both belt conveyors, each having portions in juxtaposition in a glove transfer region where the glove transfer means acts to transfer the gloves from the first belt conveyor to the second belt conveyor when the handedness of the glove needs to be changed prior to stacking.

The processing means may be connected to the glove placement means and may also be arranged to control the operation of the glove placement means in the movement of the gloves by the glove placement means away from the conveyors.

Preferably, the glove placement means includes a glove manipulator that comprises a lifting portion for lifting each of the moved gloves from the first and second conveying means. The lifting portion preferably also serves to deposit the glove at a stacking station, in which case the lifting portion is a lifting and depositing portion of the glove manipulator.

The glove manipulator may include an electrostatic generator for applying an electrostatic charge to the lifted glove in order to adhere this glove to the lifting and depositing portion. The glove manipulator may, however, comprise additionally or alternatively a pneumatic system for sucking the glove to the lifting and depositing portion and preferably also for depositing the glove.

Preferably, the lifting portion of the glove manipulator is an underside or lowermost portion of the glove manipulator.

The lifting and depositing portion may comprise means for depositing each lifted glove, for example when moved into position with a stack of gloves built up during previous cycles of lifting and depositing gloves.

Preferably, the glove manipulator comprises means for rotating the lifted glove about an axis, which will most commonly be a vertical axis, parallel with a stacking axis of the deposited gloves.

When the glove is in position for depositing, the glove may then be dropped on top of a stack of gloves being built up by the glove stacking apparatus. Together with the flipping of gloves by the transfer interaction between the first and second conveying means, the facility to rotate a lifted glove about a vertical axis enables the apparatus to position each glove in a desired orientation. In particular, this permits control of the orientation of both the thumb and the cuff of each glove deposited in the stack. For example, each deposited glove can be oriented in the same manner, for example with cuffs and thumbs of adjacent gloves all similarly oriented, or in alternate orientations, for example, interfolded so that a glove dispensed from a dispensing container serves to pull partially out from the dispenser the next glove to be dispensed.

The first and second conveying means may be belt conveyors, each glove being held conformally against the second and/or first conveys and against a lifting surface of the lifting portion as the gloves are moved and positioned by the apparatus prior to depositing for stacking. Ideally the gloves are flattened with fingers and thumb being splayed apart in order to compact the volume of the stacked gloves as far as practicable.

The glove transfer means may comprise an electrostatic generator for applying an electrostatic charge to the transferred glove in order to adhere said transferred glove electrostatically to the second conveyor loop. The glove transfer means may, however, comprise either additionally or alternatively, a vacuum pneumatic system for transferring gloves to the second conveyor loop.

The glove placement means may be used in a method of stacking gloves in a desired orientation with respect to each other, comprising the steps of:
  using a glove transport means comprising a first conveying means and a second conveying means such that gloves are transported along said first conveying means towards said second conveying means;
  using a sensing apparatus to sense the orientation of each of said transported gloves transported by the first conveying means;
  using a processor to determine from said sensed orientation whether or not the sensed orientation of said glove is in a desired orientation for removal from the first conveying means prior to stacking of said glove;
  using a glove transfer means to transfer said transported gloves from the first conveying means to the second conveying means when said sensed orientation is not a desired orientation;
  using the second conveying means to transport said transferred gloves;
  wherein said transfer and subsequent transport of said gloves by the second conveying means has the effect of changing the orientation of said gloves to a desired orientation for removal from the second conveying means prior to stacking of said glove.

If the sensed orientation of a glove transported by the first conveying means is correct, then the glove is removed from the first conveying means for stacking in a stack of gloves. On the other hand, if the sensed orientation of a glove transported by the first conveying means is incorrect, then a glove transfer means is used to transfer the glove from the first conveying means to the transporting surface of the second conveying means.

Preferably, the first conveying means transports gloves in a first direction, the second conveying means having a transporting surface in opposition to the first conveying means and moving in the same first direction of travel as the first conveying means.

The sensing apparatus may then sense the orientation of each transported glove with respect to this first direction of travel.

The transporting surface of the second conveying means may be moved in a loop so that this transporting surface transports the transferred gloves in a second direction opposite to the first direction so that the orientation of transferred gloves transported by the transporting surface is transformed into a desired orientation for stacking.

The glove placement means may be also be used in an apparatus having a glove transport means for handling gloves to be stacked, comprising at least two glove conveyors for transporting said gloves and a glove transfer means, said conveyors including a first conveyor and a second conveyor, the first conveyor leading to the second conveyor and the glove transfer means being operable to transfer said transported gloves from the first conveyor to the second conveyor, the second conveyor having a conveying surface, a glove transfer portion of said surface being permeable to air flow through said surface, wherein the glove transfer means includes a source of vacuum air pressure and means to control the application of said vacuum air pressure through said permeable glove transfer portion of said conveying surface in order to control the transfer of gloves from the first conveyor to the second conveyor.

The second conveyor may include a roller around which said conveying surface passes, the roller including at least one air flow channel and the vacuum air supply being applied to said permeable glove transfer portion through said at least one air flow channel.

The least one channel may include an array of perforations in an outer surface of the roller.

The conveying surface is preferably a mesh, said mesh being permeable to the air flow.

The glove placement means may include an apparatus for manipulating gloves presented flat for stacking by a transporting surface, comprising a glove manipulator comprising a lifting portion, said lifting portion having a downwardly directed surface for lifting each of said moved gloves from said transporting surface, and a means for attracting said lifted glove to said downwardly directed surface in order to hold said lifted glove to said downwardly directed surface of the lifting portion as gloves are manipulated for stacking.

In one embodiment, the means for attracting a lifted glove to the downwardly directed surface comprises an electrostatic generator for applying an electrostatic charge to a lifted glove in order to adhere the lifted glove to the downwardly directed surface of the lifting portion.

In another embodiment, the means for attracting a lifted glove to the downwardly directed surface comprises a pneumatic system for applying a vacuum to a lifted glove in order to adhere the lifted glove to the downwardly directed surface of the lifting portion.

In one embodiment, the glove placement means comprises a ground plate to which the electrostatically charged glove is attracted. In one embodiment, the apparatus includes a plurality of insulating strands strung over and separated from the ground plate, the strands serving in use to support and separate the electrostatically charged glove from the ground plate. In another embodiment, an insulating plate has a plurality of perforations through which the electrostatically charged glove is attracted to the ground plate, the insulating plate serving in use supporting and separating the electrostatically charged glove from the ground plate.

Preferably, the lifting portion has means for discharging the electrostatic charge on the glove prior to said depositing of the glove. Once the electrostatic charge has been discharged, the glove will either fall from the lifting portion or can be readily assisted to fall, for example with a puff of compressed air applied to the interface between the lifting and depositing portion and the glove.

The lifting and depositing portion may have means for increasing the separation between the charged glove and the ground plate in order to lessen the electrostatic attraction between the glove and the ground plate prior to dropping the glove for stacking. These means may include one or more pins that project downwards of the lifting means, most preferably in areas not covered over by lifted gloves.

The glove placement means may be used as part of a glove stacking apparatus, comprising a recess in a work surface. The glove placement means is then arranged to deposit glove above the recess for stacking within the recess. The recess may have side walls for aligning gloves stacked one on another inside the recess and a movable floor which can be lowered as said stack of gloves grows so the topmost glove in the stack of gloves is substantially level with the work surface, wherein the apparatus comprises at least one movable flap adjacent an edge of said recess for folding towards the recess a portion of a glove overlapping said edge of the recess.

The flap is preferably hinged adjacent the edge of the recess.

Gloves are preferably deposited at the recess such that a portion of the glove is contained by said recess and another portion of said glove overlaps an edge of said recess and lies on said at least one movable flap. The movable flap is then moved to fold towards the recess the portion of the glove that overlaps the edge of the recess so that the glove is contained by the recess. During this process, the flap preferably contacts the stack of gloves formed in the recess in order to help compress the stack of gloves.

The recess may be substantially square or rectangular. There may also be a pair of flaps on opposite side edges of the recess for folding alternately inwards to the recess, portions of gloves overlapping alternately one or another of the opposite side edges of the recess.

The glove placement means may therefore be used in a method of stacking gloves using a glove stacking apparatus, comprising the steps of:
i) moving the movable floor proximate the level of the work surface;
ii) placing a first glove to be stacked over the recess, with a first cuff portion of said glove overlapping an edge of the recess;
iii) placing a second glove to be stacked over the recess, with a second cuff portion of said glove overlapping an edge of the recess;
iv) lowering the recess floor as required to keep the top of the stack of gloves in the recess substantially level with the work surface;
v) using at least one movable flap to fold over said first cuff portion inwards towards the recess, so that the first cuff portion is folded over a finger portion of the second glove contained within the recess; and
vi) repeating steps ii) to v) to build up a stack of interfolded gloves within the recess.

The packing recess may be used with at least one movable flap for folding towards the recess a portion of a glove overlapping said edge of the recess.

The movable flap preferably has a surface that is permeable to air flow through said surface, the glove stacking apparatus including a source of vacuum air pressure and means to apply said vacuum air pressure through said permeable surface of the movable flap in order to pull said overlapping portion of said glove to the flap prior to folding of said overlapping portion.

The source of vacuum pressure is separate from the flap so that as the flap folds towards the recess, the application of the vacuum air pressure through the permeable surface is automatically released.

The means to apply said vacuum air pressure may comprise at least one perforation in a work surface beneath the permeable surface of the movable flap, and most preferably comprises a plurality of such perforations.

The source of vacuum pressure is preferably arranged to provide a steady vacuum pressure. The application of the vacuum air pressure through the permeable surface then depends on the degree of separation between the movable flap and the means to apply said vacuum air pressure through said permeable surface of the movable flap. As the flap moves towards the recess, the vacuum pressure is therefore automatically released.

Preferably, the, or each, flap is arranged to fold towards the recess such that, in use, the flap contacts the stack of gloves formed in the recess in order to help compress the stack of gloves.

The permeable surface of the flap is preferably a mesh, this mesh therefore being permeable to the air flow.

BRIEF DESCRIPTION OF THE DRAWINGS

The invention will now be further described, by way of example only, and with reference to the accompanying drawings, in which.

DETAILED DESCRIPTION

Figure 1:
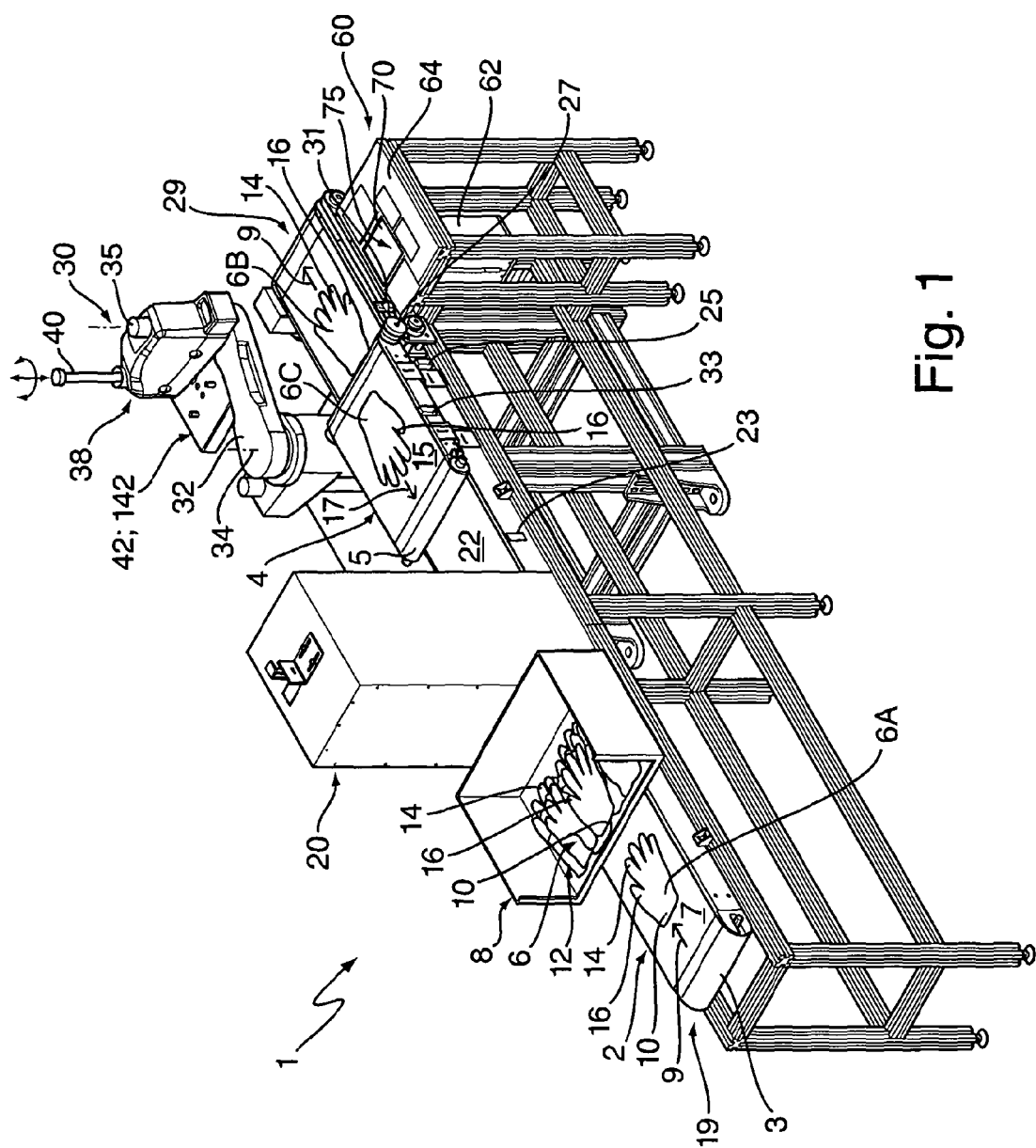
FIG. 1 is perspective view of an apparatus for stacking ambidextrous gloves including a glove placement means for moving gloves to be stacked, according to a first preferred embodiment of the invention, showing how gloves are transported by a first conveying means, past a machine vision system towards a second conveying means to which gloves may be transferred to reverse the handedness of the orientation of the glove with respect to a glove placement means.
Figure 2:
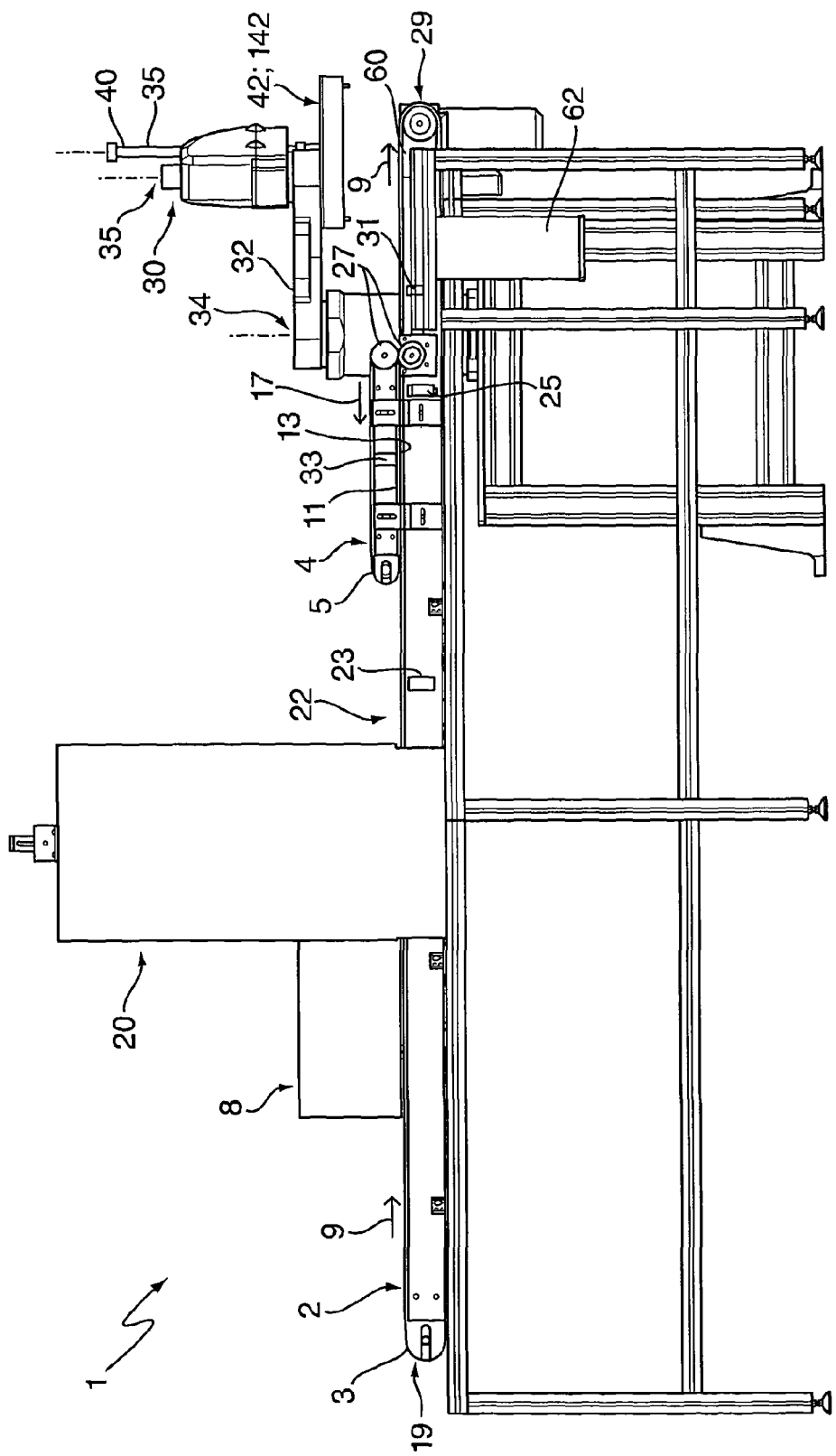
FIGS. 2 and 3 are, respectively, side and top views of the apparatus of FIG. 1.
Figure 3:
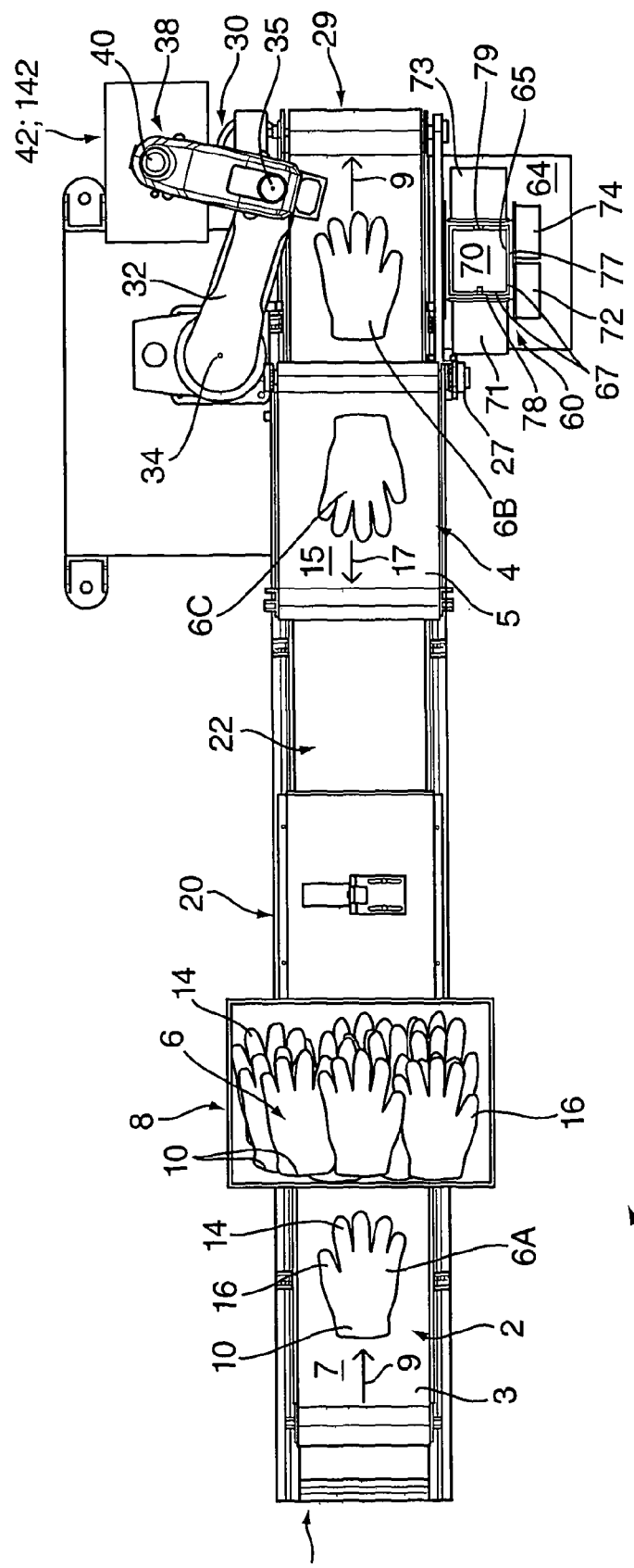
Figure 4:
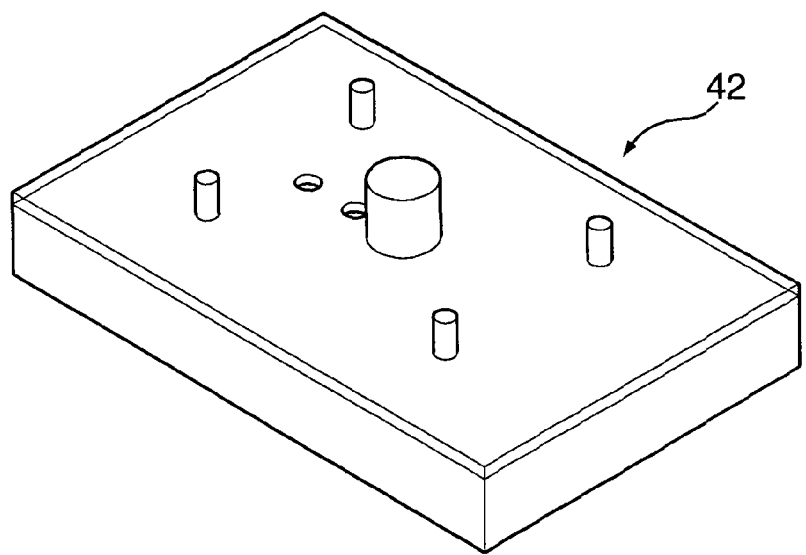
FIG. 4 is a perspective view of a first embodiment of a glove placement means having a glove manipulator for lifting gloves from the conveyors and, if necessary, for rotating the orientation of the glove about a vertical axis prior to depositing on a stack of gloves.

FIGS. 1 to 3 show various views of a glove stacking apparatus 1 for stacking gloves with the thumbs in a desired orientation. The apparatus comprises a first conveying means in the form of a first conveyor 2 and a second conveying means in the form of a second conveyor 4. Both the first and second conveyors have straight loops of belt 3, 5, with an upper surface 7 of the first conveyor 2 travelling in a first direction indicated by arrow 9. The second conveyor 4 lies atop the first conveyor 2 with a lower portion 11 of the second conveyor belt 5 being opposed to a transfer portion 13 of the first conveyor belt 3, these portions 11, 13 being separated by about 1 mm and moving at matched speeds in the same direction 9 so that an upper surface 15 of the second belt 5 moves in a second direction 17 opposite to the first direction 9.

A supply of gloves 6 held within a bin 8 is brought to the vicinity of an upstream end 19 of the first conveyor 2. The gloves 6 in the bin 8 are not fully ordered but preferably have a cuff end 10 facing towards an open side 12 of the bin 8, which is positioned above the upper surface 7 of the first belt 3.

The gloves 6 in the bin are oriented with the glove fingers 14 and thumb 16 facing generally in a direction parallel with the first direction of motion 9 of the first conveyor 2. A worker (not shown) may then reach into the open side 12 of the bin 8 and get hold of a glove 6 by the cuff 10 and pull the gloves in the second direction 17 one at a time onto the upper surface 7 of the first belt 3, such that the fingers drag along the first belt upper surface 7.

In doing this, the opposite motions of the gloves 6 and first belt 3 will tend to pull the fingers 14 and thumb 16 of each glove flat with the belt. In the embodiment of the invention, the gloves 6 are disposable ambidextrous medical inspection gloves, although the invention is applicable to other types of hygienic glove. It is not necessary for the thumbs 16 to be positioned on either the right or the left of the glove, as viewed in the direction of motion 9. A machine vision sensing device 20 under the control of a microprocessor (not shown) is used to capture from above an image of each glove 6A placed on the upstream end 19 of the first belt 3. The machine vision sensing device 20 is not described or shown in detail but may include a camera or other light sensing means, a source of illumination such as a flash lamp, one or more scanning or static laser beams or a light curtain.

The processor determines from the captured image if the thumb 16 is on the left or right of the glove 6A and also determines if there is a problem with the orientation of the glove, as may be the case if the fingers 14 or thumb 16 are not splayed outwards and are overlapping, or if the cuff 10 is over-folded or under-folded.

The gloves 6A then pass to a rejection region 22 of the apparatus. The first belt 3 is a mesh fabric belt having holes of about 4 mm in size. The fabric preferably has insulating properties, for example being formed from a PTFE fabric material. Beneath the rejection region 22 is a valve 23 connected to a source of compressed air (not shown) which under the control of the processor sends a blast of air upwards and to one side of the first belt 3 to eject a misaligned glove off and to one side of the belt, where such rejected gloves are caught by a recycle bin (not shown) for subsequent recycling through the glove stacking apparatus 1.

If the gloves are to be stacked in a regular way, and if the gloves are randomly placed on the first belt 3, with the thumb 16 either to the left or the right relative to the direction of motion, then the processor will determine, on average, that 50% of the gloves are in a correct orientation for stacking, and 50% are not. In the illustrated example, one glove 6B has reached the vicinity of a downstream end 29 of the first conveyor 2. This glove has been determined by the processor to be correctly oriented for stacking. Another glove 6C is shown on the upper surface of the second belt 5. This glove 6C was found by the processor to be in the incorrect orientation for stacking by the processor when on the first belt 3 and has been transferred from the transfer portion 13 of the first belt 3 to the lower portion 11 of the second belt 5, prior to being conveyed by the loop of the second belt onto the upper surface 15 of the second conveyor 4. This operation has the effect of flipping the glove 6C through 180° around a horizontal axis at right angles to the direction of motion 9 of the first conveyor 2, such that the handedness of each of the gloves 6C transferred to the second conveyor 4 is reversed from a left handed orientation to a right handed orientation or alternatively from a right handed orientation to a left handed orientation as the second conveyor transports the gloves. As will become clear from the explanation below, this then positions the illustrated glove 6C in a correct orientation for stacking.

It should be noted that the first and second belts 3, 5 in the region 11, 13 where these overlap move at the same speed and direction 9 with synchronicity being maintained by a 1:1 drive belt and pulley arrangement 27 connecting the first and second conveyors 2, 4.

The glove stacking apparatus 1 also comprises a glove placement means 30, which is here an articulated robot arm 32 that extends away from a first vertical axis pivot 34 towards a second vertical axis pivot 35 on which a glove manipulator 38 is pivotably mounted. In addition to being pivotable about the second pivot 35, the manipulator has a vertical and rotational axis movement mechanism 40 that extends downwards to an attractive lifting and depositing portion 42 of the glove manipulator 38, a first and a second embodiment 42, 42' of which using electrostatic attraction are illustrated in FIGS. 4 to 10 and 1 third embodiment of which 142 using a vacuum, or negative pressure, supply is shown in FIGS. 11 to 19.

As will be explained in more detail below, the glove manipulator 38 moves the lifting and depositing portion 42, 42' so that this is above the next glove to be stacked, and then lifts and moves this glove either from the first conveyor 2 or the second conveyor 4 and deposits this to one side of the downstream end 29 of the first belt 3 at a stacking station 60, where the glove 6B, 6C is deposited for stacking.

The gloves 6C are transferred from the first to the second conveyors by means of a static electricity generator 25 comprising a static generating bar positioned beneath the portion 13 of the first belt 3 opposite the second belt 5. The charge passes through the air and holes in the first belt mesh to charge up the glove 6C to be transferred. The second belt 5 is a mesh with an insulating outer surface and with a ground plate (not shown) behind in the region where the glove is transferred. Gloves 6C once charged are therefore initially electrostatically attracted to the second belt 5 and leave the first belt 3, which also has an insulating outer surface, to travel around the loop of the second belt 5 to reach the upper surface 15 of the second conveyor 4. A second static charge electricity generator 33 comprising a static generating bar positioned beneath the upper surface 15 of the second belt 5 then recharges the glove. The charge passes through the air and holes in the first belt mesh to re-charge up the glove 6C. There is no ground plate behind the mesh of the second belt in this region, and so the glove is free to be attracted to another ground surface, which as explained below is provided in the lifting and depositing portion 42, 42'.

The lifting and depositing portion 42, 42' of the glove placement means 30 is synchronized with the continuous motion of the belts 3, 5 and under the control of the same processor registering the location and portion of each glove 6A by means of the machine vision system 20. Alternatively, it would be possible to have a second machine vision system (not shown) to register the position and of the gloves 6B, 6C ready for stacking. It should be noted that in the drawing, both gloves 6B and 6C are shown for purposes of illustration only in position ready for lifting the by the lifting and depositing portion 42, 42'. Because the belts 3, 5 move continuously at a constant speed, preferably about 300 mm per second, in operation, only one of the illustrated gloves 6B, 6C would be positioned ready for lifting at any one time.

The lifting and depositing portion 42, 42' then moves into position above the glove 6B, 6C to be lifted. The lifting and depositing portion is rectangular, and is rotated by the movement mechanism 40 so that the long axis of the rectangle is aligned with the long axis of the glove. If the long axis of the glove 6B, 6C is not aligned exactly with the length of the belts 3, 5, then this is detected by the image sensing system 20 and the angle of the lifting and depositing portion 42, 42' is correspondingly adjusted by the rotational axis movement mechanism 40 to match that of the glove prior to lifting the glove from the belt 3, 5. The movement of the belts 3, 5 is continuous so the arm 32 and glove manipulator 38 match the movement of the glove 6B, 6C on the conveyor 2, 4 while the vertical axis movement mechanism 40 drops the lifting and depositing portion 42, 42' on top of the glove.

Figure 5:
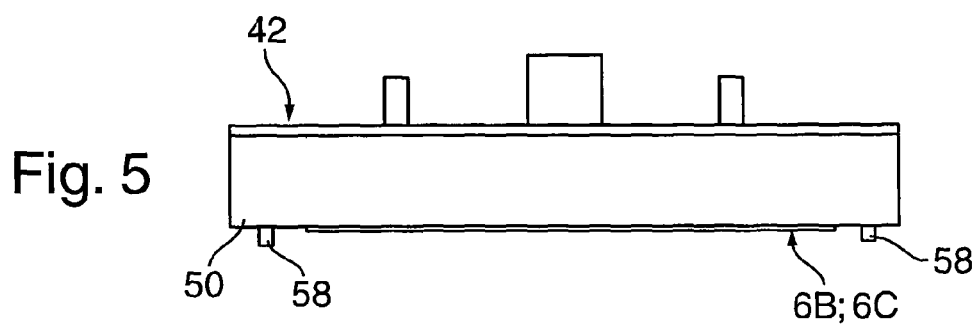
FIG. 5 is a side view of the glove manipulator of FIG. 4, showing how a glove is held electrostatically to a lowermost insulating surface of the glove manipulator.
Figure 6:
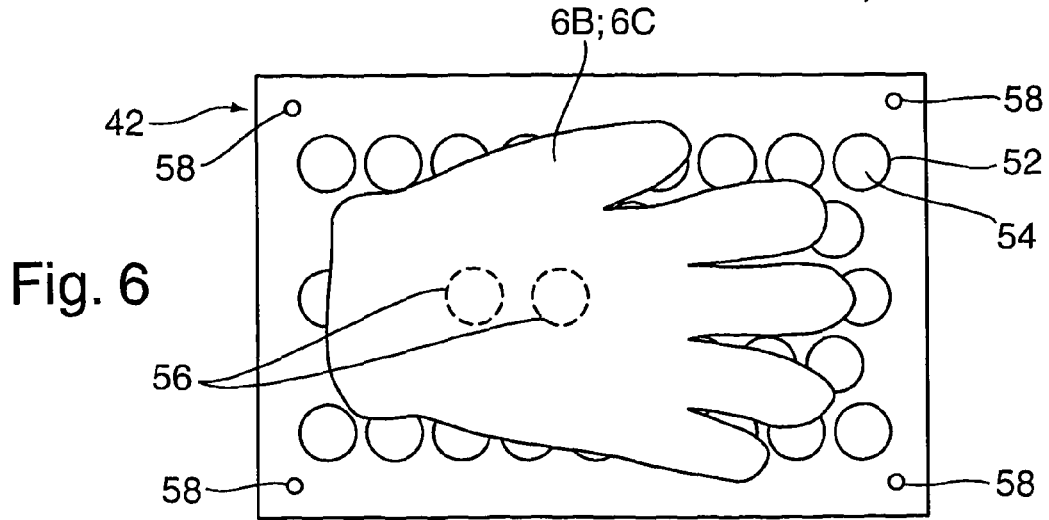
FIG. 6 is a bottom view of the glove manipulator of FIG. 4, showing how the glove is held flat against the insulating surface, which has an array of perforations behind which is a ground plate to which the glove is attracted.
Figure 7:
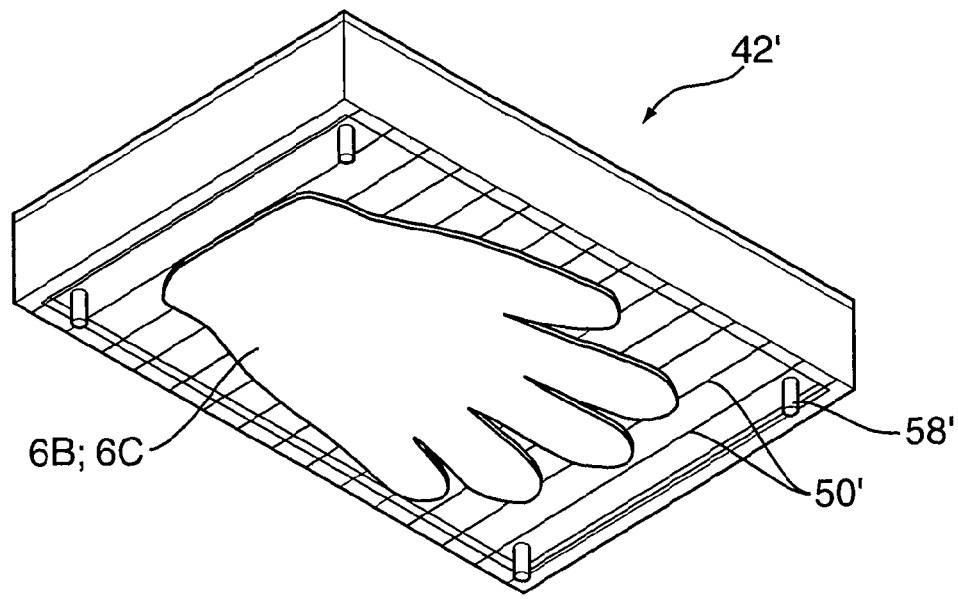
FIG. 7 is a perspective view of a second embodiment of a glove manipulator for lifting gloves from the conveyors in which the gloves held against an array of insulating strands behind which is a ground plate to which the glove is attracted.
Figure 8:
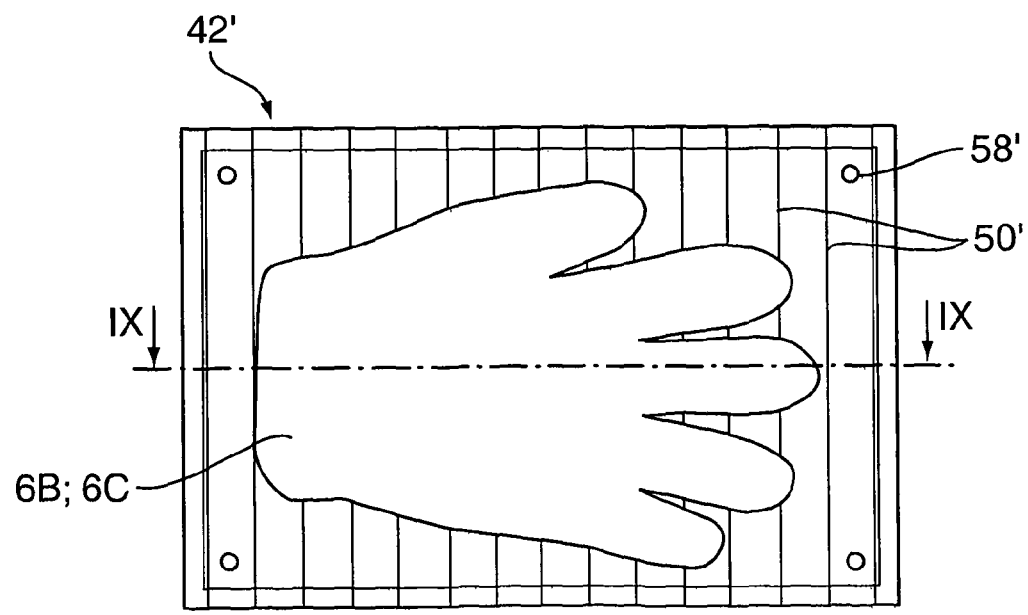
FIG. 8 is a view from beneath of the glove manipulator of FIG. 7.

As shown in FIGS. 5 and 6, the first embodiment of the lifting and depositing portion 42 has a flat under surface 50, which is made from a thin plate insulating material having an array of circular holes 52, behind which is an insulated ground plate 54. Although not visible in FIGS. 5 and 6, the ground plate 54 is covered over by a thin insulative sheet to prevent direct discharge from a charged glove to the ground plate.

The gloves 6B are transferred from the first conveyor to the lifting and depositing portion by means of a static electricity generator 31 comprising a static generating bar positioned beneath the surface of the first belt 5. The charge passes through the air and holes in the first belt mesh to charge up the glove 6B. As the lifting and depositing portion comes into proximity with the charged glove, the glove is attracted to the underside 50 of the lifting and depositing portion 42, which therefore acts as a glove lifting surface having an attractive glove lifting portion.

As the lifting and depositing portion 42 comes into proximity with the glove 6B, 6C to be lifted, the charged glove is attracted to the insulated ground plate 54 and therefore adheres to the outer plate surface 50.

The lifting and depositing portion 42 can then remove the glove 6B, 6C from the belt 3, 5 and deposit the glove at the stacking station 60. The glove is de-adhered from the lifting and depositing portion by moving the ground plate 54 away from the outer insulative layer 50. Additionally, the lifting portion also contains an electrostatic generator 56, the location of which is indicated by dashed lines, aligned with corresponding holes in the outer plate 50 and ground plate 54. This applies a charge one side of the glove which it has been found can help to collapse the glove and help the glove adhere better to the stack of glove being built up at the stacking station 60.

This ground plate is movable in a vertical direction within the lifting and depositing portion 42 and is spring biased to a downwards location nearest the outer layer 50. Four pins or studs 58 project downwards from the ground plate through the outer layer 50. When the lifting and depositing portion comes into contact with surfaces at the stacking station 60, these pins are pressed upwards thereby lifting the ground plate and thereby lessening the attraction of the glove 6B, 6C to the ground plate 54 whereupon the glove drops away from the lifting and depositing portion. Although not illustrated, if needed, the manipulator 30 may be connected to a source of compressed air which may be used to send a blast of air through the holes 52 to dislodge the glove from the outer layer 50.

Figure 9:
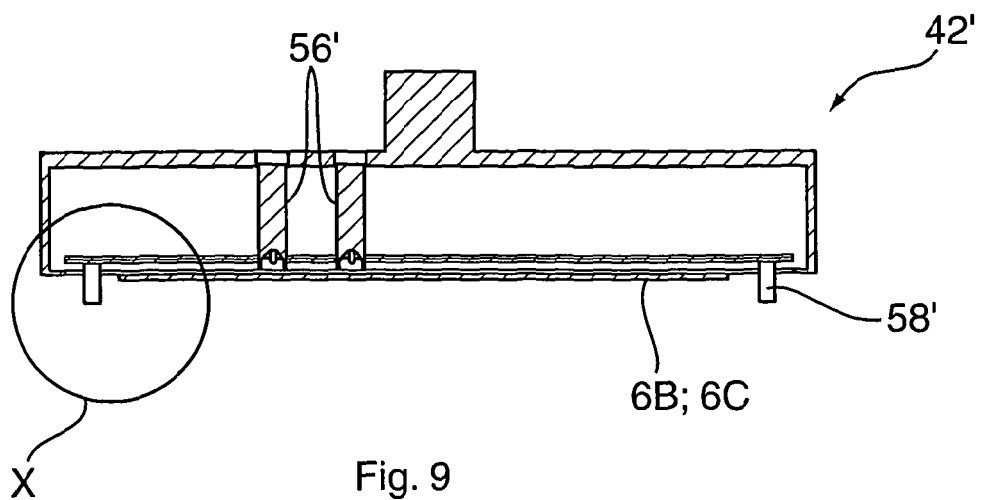
FIG. 9 is a cross-section view of the glove manipulator, taken along line IX-IX of FIG. 8.
Figure 10:
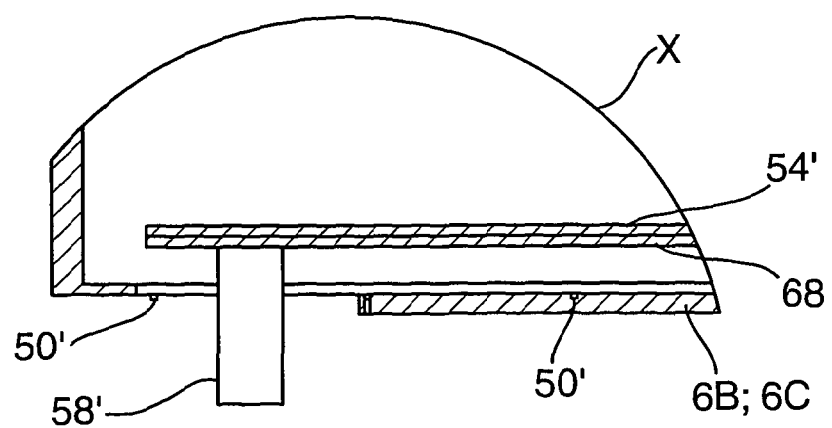
FIG. 10 is an enlarged view of a portion of the cross-section of FIG. 9 labeled X.

The second embodiment of electrostatic lifting and depositing portion 42' works in a similar manner to that described above. In this embodiment, there is no outer layer, but rather a series of parallel insulating threads or strands 50', which serve to separate the glove 6B, 6C from the ground plate 54'. FIG. 9 shows the static electricity generators 56' within the lifting portion and the enlarged cross-section view of FIG. 10 shows the insulative layer 68 on the ground plate 54'. FIGS. 9 and 10 show schematically how the glove 6B, 6C is adhered against the parallel insulating threads or strands 50'. In this case, the ground plate 54' acts as a glove lifting surface having an attractive glove lifting portion.

As with the first embodiment, the electrostatic lifting and depositing portion 42' described above has four pins or studs 58' that project downwards from the ground plate 54' through the parallel insulating threads or strands 50'. When the lifting and depositing portion comes into contact with surfaces at the stacking station 60, these pins are pressed upwards thereby lifting the ground plate and thereby lessening the attraction of the glove 6B, 6C to the ground plate 54' whereupon the glove drops away from the lifting and depositing portion.

The packing station 60 shown in FIGS. 1 to 3 will now be described in more detail. The packing station 60 has a packing sleeve 62, inset in a work surface 64. The packing sleeve 62 extends vertically and has a substantially rectangular horizontal cross-section with rounded corners. The sleeve is formed from folded sheet metal, preferably stainless steel.

The packing sleeve 62 contains a movable base 70 that provides a floor surface and that is slightly recessed to provide a shallow receptacle 75 for receiving gloves being stacked. Prior to stacking of gloves, the floor 70 is initially substantially at the level of the work surface 64 or recessed slightly, for example recessed by between 10 mm to 25 mm. As gloves are stacked on the floor, the movable base 70 drops so that the topmost stacked glove remained substantially at, or just below, the level of the work surface 64. The next glove to be stacked then lies flat above the previously stacked gloves and surrounding work surface 64.

The sleeve walls 65 and base 70 define a recess or receptacle the cross-section of which is less than the flattened extent of the gloves 6B, 6C. Portions of the gloves to be stacked therefore overlap edges 67 of the receptacle. In this example, the receptacle 75 is sized such that when the glove fingers 14 are aligned within the receptacle, the glove cuffs 10 will initially extend beyond the bounds of the receptacle. The packing station therefore contains two movable and generally rectangular or square flaps 71, 73, arranged on opposite sides 78, 79 of the receptacle 75 which initially lie flat or flush with the work surface 64. Each flap is pivoted along a straight edge nearest the receptacle, with one of each pair being on adjacent sides of the receptacle so that the paired flaps can fold inwards the overlapping portions of each glove from adjacent sides.

In use, a glove is placed with the finger portions 14 being fully within the confines of the side walls 65 and with the thumb 16 being on the right hand side of the receptacle 75, as viewed in the first direction 9. Optionally, there may be two additional movable and generally rectangular or square flaps 72, 74 on a "thumb" side 77 of the receptacle between the two opposite sides 78, 79. Each of these flaps 72, 74 is pivoted along a straight edge nearest the receptacle. In the event that the thumb 16 extends beyond the bounds of the receptacle, the thumb 16 may be first folded over by one of the flaps 72, which then returns to lie flush with the work surface 64.

The next glove is then positioned on top of the first glove, with the finger portions 14 again being fully confined by the side walls but oriented at 180° to the first glove so that the cuffs of the first two gloves extend away from one another and overlap opposite sides 78, 79 of the receptacle 75. The thumb 16 is first folded over by one of the flaps 74, which then returns to lie flush with the work surface 64.

The cuff 10 of the first glove to be placed on the work surface 64 is then folded over the finger portion 14 of the second glove, using the other one 71 of the pair of flaps, which then returns to lie flush with the work surface. The thumb 16 may then be first folded over by one of the flaps 72, which then returns to lie flush with the work surface.

If there are no flaps 72, 74 to fold in thumbs, then the thumbs will gradually fall into the receptacle 75 as the base floor 70 is lowered.

A third glove is then placed on the second glove, in the same orientation as the first glove was placed.

The cuff of the second glove to be placed on the work surface 64 is then folded over the finger portion of the third glove, using the other one 73 of the pair of flaps, which then returns to lie flush with the work surface.

In this way an interfolded stack of gloves for cuff first dispensing from a box dispenser, can be built up automatically. During dispensing, the cuff of the glove being dispensed is gripped and removed from a container (not shown), and as the fingers of that glove are pulled out of the container, the fingers of that glove pull out the cuff of the next glove for dispensing.

When sufficient gloves have been stacked in the receptacle, for example between about 100 and 150 gloves, the stacking operation is paused, and the receptacle 75 is removed from the packing station 60, either automatically or manually, and an empty receptacle is put in place at the packing station, and the operation described above is repeated.

Although not illustrated or described in detail herein, once the gloves are stacked in the receptacle, the stacked gloves may be packed in a box dispenser by placing an open mouth of the box over the receptacle and moving the base 70 upwards to press the stacked gloves into the open box, which may then be closed and sealed.

FIGS. 11 to 17 show various views of a second embodiment of an apparatus 101 for stacking ambidextrous gloves, according to a second preferred embodiment of the invention. In the second embodiment, features similar to those of the first embodiment are indicated by reference numerals incremented by 100.

The second embodiment includes a machine vision sensing device (not shown) the same as that described above and has first and second conveyors 102, 104 that present gloves to a glove placement means 130 in the same manner as described above.

The second embodiment 101 differs from the first embodiment 1 in that there is no use of electrostatic transfer means. Instead, a vacuum air supply (not show) is used in the transfer of gloves from the first conveyor 102 to the second conveyor 104, and is also used to hold a glove to the underside 150 of a pneumatic lifting and depositing portion 142 of the glove manipulator 138. In this example, the underside 150 of the lifting and depositing portion 142 acts as a glove lifting surface having an attractive glove lifting portion. The vacuum air supply is connected to an air outlet connection 80 at one end of a cylindrical roller 81 in the second conveyor 104 around which gloves 106C must pass to reach the upper surface 115 of the second mesh belt 105. The roller 81 is hollow (not shown) and has a number perforations 83 across its width and around its circumference so that when the hollow interior of the roller is connected to the air outlet 80 a vacuum air pressure at the outlet causes air to be sucked through the perforations. This causes a glove 106C on the first mesh belt 103 to be transferred to the second belt 105 at the roller 81.

Prior to this transfer, the glove 106C is retained to the first mesh belt 103 by a similar vacuum supply that sucks air through the first belt to keep the glove 106C flat on the belt and so the glove can be conveyed without interference in a 1 mm to 2 mm gap 96 between the belts 103, 105. When a glove is to be transferred to the second conveyor 104, the vacuum air supply to the first belt is stopped at the same time as the vacuum air supply to the roller 81 is started. When a glove is not to be transferred to the second conveyor 104, the vacuum air supply to the first belt 103 is maintained and the vacuum air supply to the roller 81 is kept off, so that the glove is conveyed by the first conveyor 102 past the transfer region between the first and second belts. In this case, to ensure that the glove clears the second belt 105, the vacuum air supply through the mesh of the first belt 103 is preferably provided underneath and beyond the second conveyor 104. Not shown are valves and a control system linked to the processor for synchronizing the operation of the vacuum air supply to the first belt and the second belt roller with the rest of apparatus.

Figure 11:
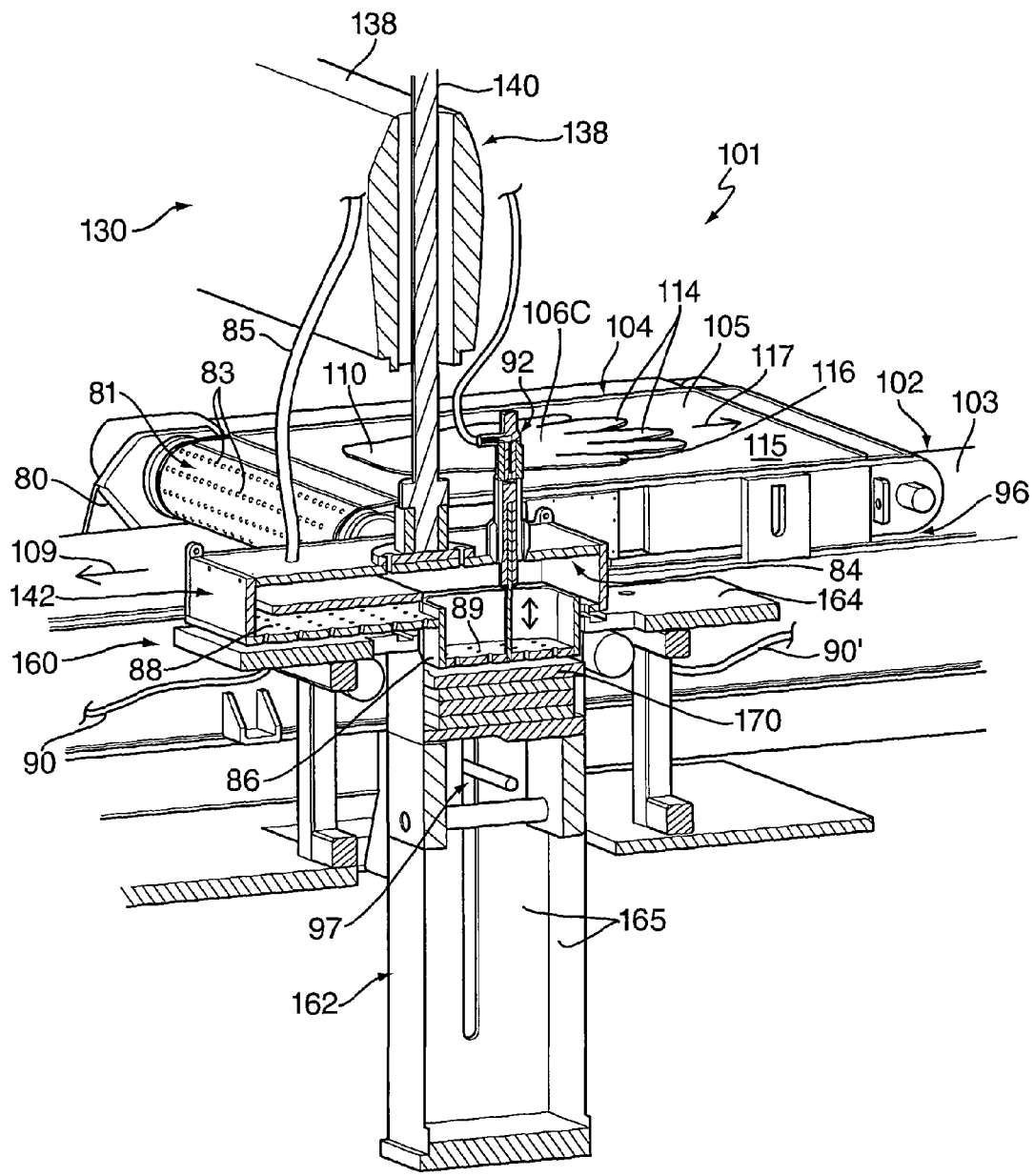
FIG. 11 is a perspective view, partly cut-away, showing part of an apparatus for stacking ambidextrous gloves including a glove placement means for moving gloves to be stacked according to a second preferred embodiment of the invention, similar to the first but using a vacuum air supply for transferring gloves to the second conveyor and for holding gloves to the underside of a glove manipulator.
Figure 13:
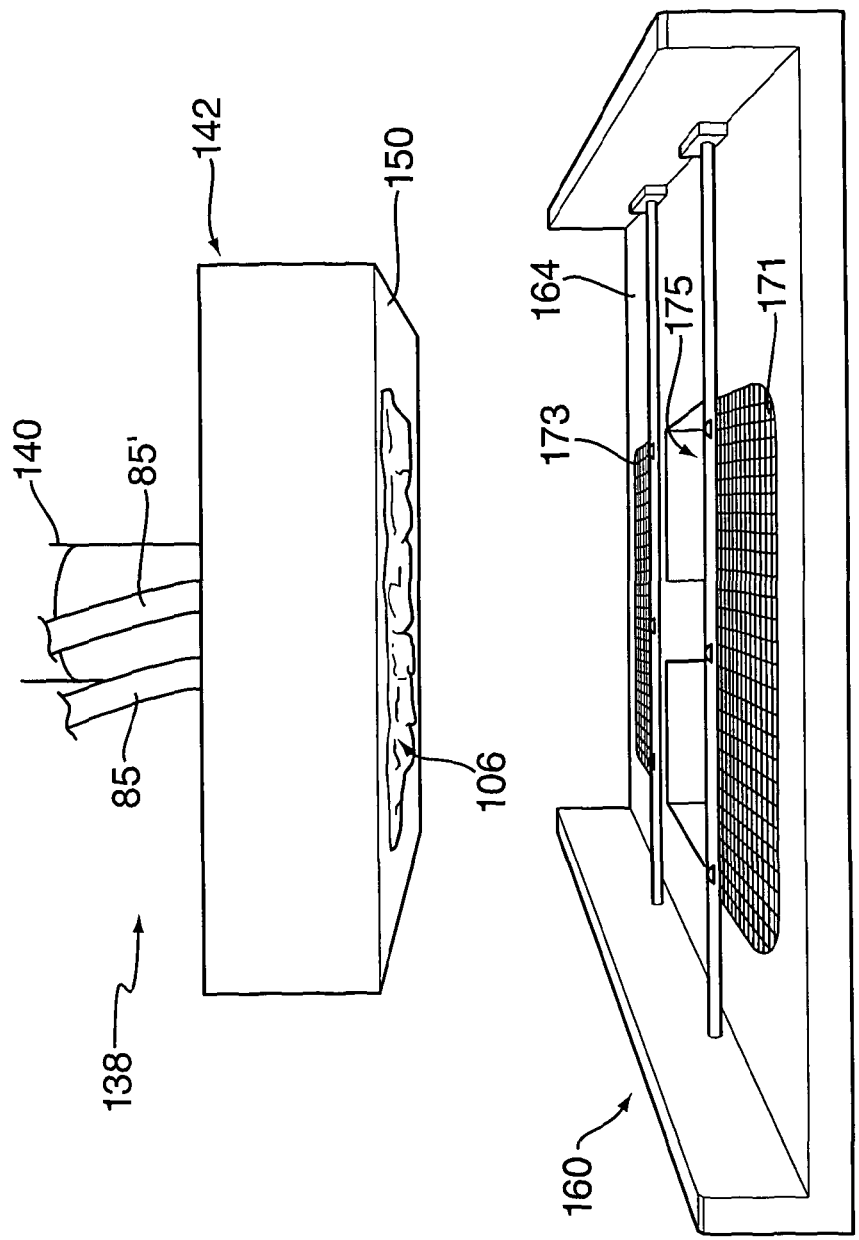
FIG. 13 is a perspective view of the packing station of FIG. 12 with the glove manipulator ready to deposit a first glove at the packing station.
Figure 15:
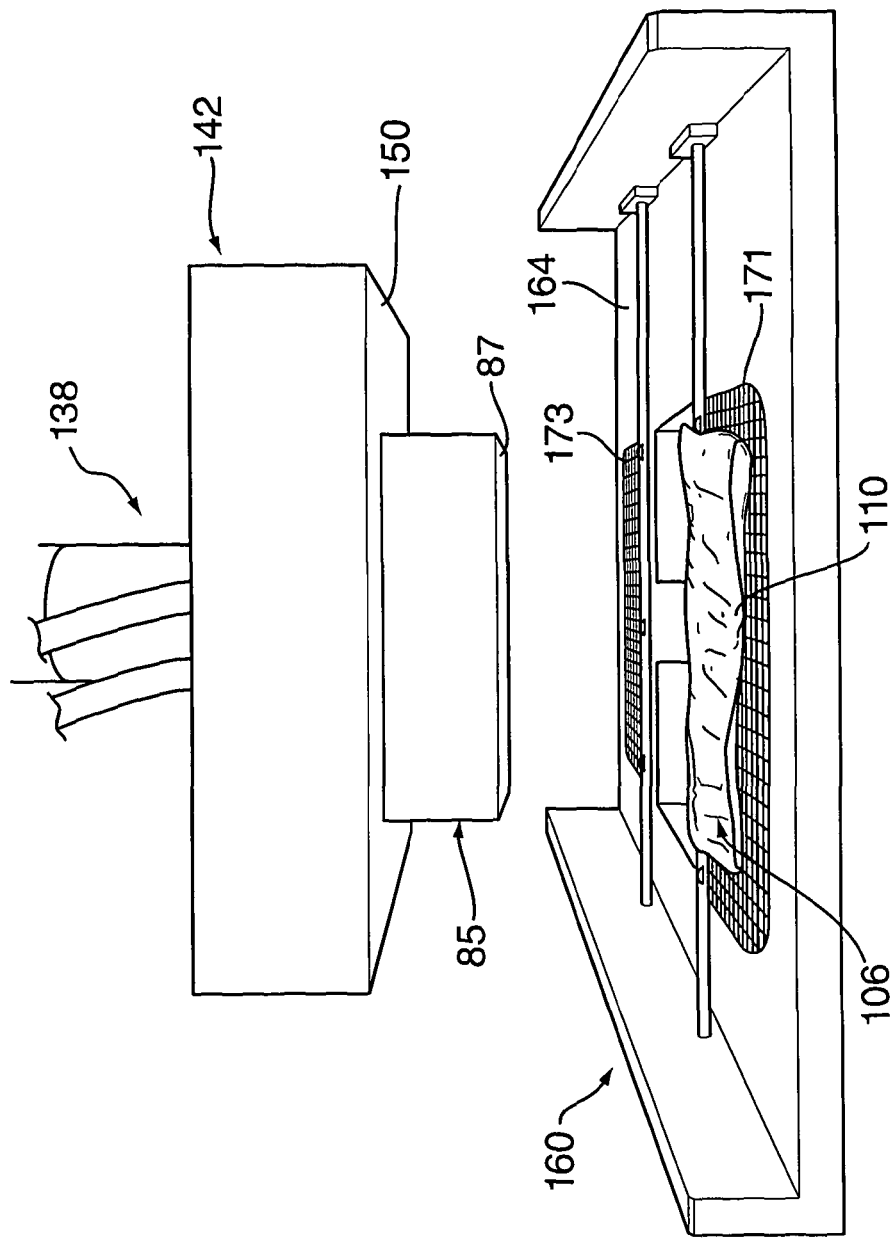
FIG. 15 shows the packing station of FIG. 14 when the glove manipulator has been withdrawn from the packing station to collect a second glove.

The lifting and depositing portion 142 has an internal pressure chamber 84 which is supplied by one or two air hoses 85, 85' connected to another air supply via control valves (not shown) which can provide either negative or positive air pressure relative to ambient air pressure. Air passes in to or out from the air chamber through perforations 88 in a flat main plate 150 on the underside of the lifting and depositing portion 142. A downwardly acting piston 86 is provided in a portion of the main plate 150. The main plate is generally rectangular with a long axis extending in the same directions as the direction of movement 109, 117 of the first and second conveyors 102, 104 when the lifting and depositing portion 142 is oriented to collect or deposit gloves. The piston 86 has a flat lower plate 87 which is co-planar with the surrounding main plate 150 when the piston is raised as shown in FIG. 13, and which extends below the plane of the main plate when extended, as illustrated in FIGS. 11 and 15. Both the main plate 150 and the piston plate 87 have a two-dimensional array of perforations 88, 89 subject to the same air pressure from the air chamber 84.

Figure 14:
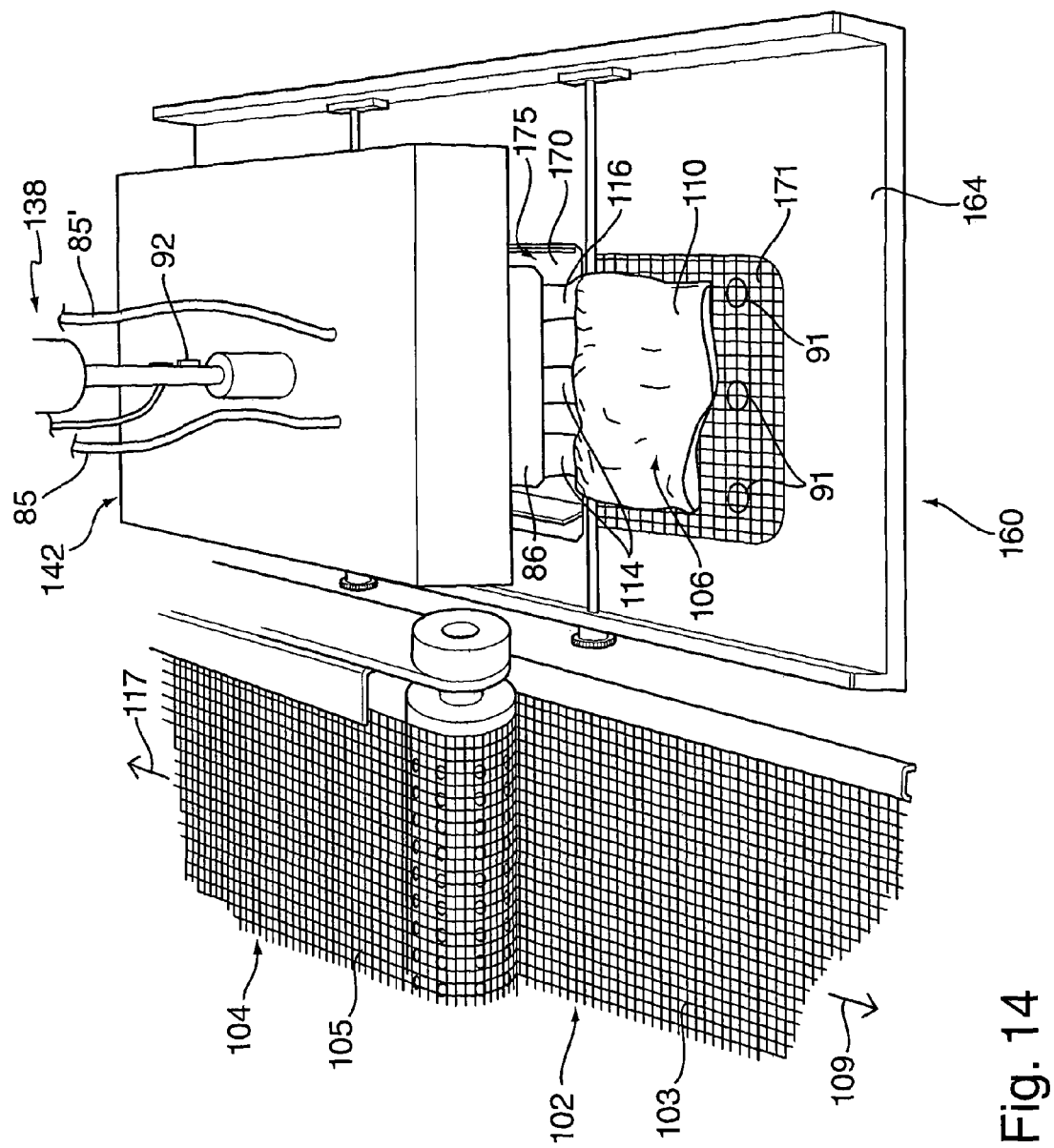
FIG. 14 is a view of the glove manipulator of FIG. 12 after depositing of the first glove at the packing station, showing how a movable member in the form of a plunger descends from beneath the glove manipulator to press a finger portion of the glove into a packing recess.

If the gloves are to be stacked with the cuffs 110 all facing one way, then the piston 86 is preferably off-centre to one end of the rectangular main plate 150, as shown in FIG. 11. If, however, the gloves are to be stacked with the cuffs alternating in opposite directions, then the piston is preferably centered in the main plate 150, as shown in FIGS. 13, 14 and 15. In both cases, when a glove is picked up by the lifting and depositing portion 142 a vacuum or negative pressure is applied to the chamber 84 as the main plate 150 is brought down against a glove on one of the conveyors. The air flow into the perforations then pulls the glove off the conveyor and onto the under surface of the lifting and depositing portion 142. The glove is preferably picked up with the finger portion 114 (which include the thumb 116), in contact with the retracted piston lower plate 87 and with the cuff portion adhered by the vacuum to the adjacent main plate 150.

Figure 12:
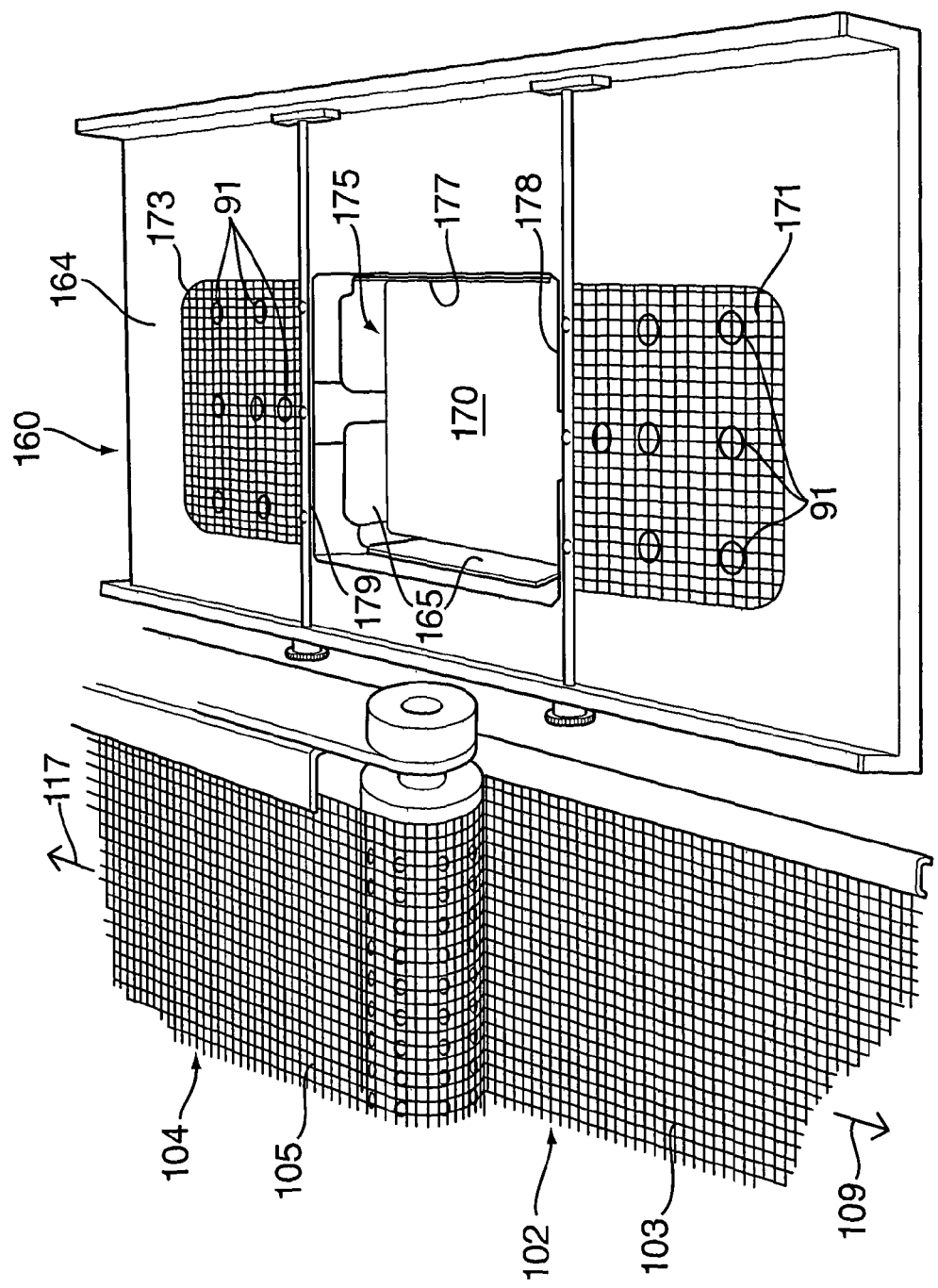
FIG. 12 is perspective view of the first and second conveyors of FIG. 11 and an adjacent packing station prior to stacking of gloves by the glove placement means.

FIG. 12 shows the adjacent packing station 160 prior to stacking of gloves by the glove placement means 130 in the packing receptacle 175. FIG. 13 shows the glove manipulator 138 positioned ready to deposit the first glove 106 in the packing receptacle 175, with a negative pressure being supplied to the internal chamber 84 through an air supply line 85.

FIG. 14 is a view of the glove manipulator 138 after depositing of the first glove at the packing station 160, showing how the piston 86 descends from beneath the lifting and depositing portion 142 to press a finger portion 114, 116 of the glove 106 into the packing recess 175. When the lifting and depositing portion 142 is ready to deposit the glove 106, the vacuum from air line 85 is switched off and a positive pressure is supplied to the internal chamber 84 through air line 85'. At the same time, a negative pressure is continuously provided through other air lines 90, 90' (see FIG. 11) which lead to an array of perforations 91 in a work surface 164 beneath two movable and generally rectangular or square PTFE mesh flaps 171, 173, arranged on opposite sides 178, 179 of the receptacle 175. In this way, the glove 106 is both pushed off and pulled from the lifting and depositing portion 142. This pneumatic action of the apparatus helps to press the glove flat against the surfaces of the packing station 160. It will generally still be the case, however, that air is trapped inside the glove, particularly the glove finger portion 114, 116.

Before the lifting and depositing head is withdrawn upwards, the piston 86 is therefore actuated downwards by means of a pneumatically driven actuator 92 to compress the finger portions of the glove 106. This pressure helps to drive out air trapped inside the glove, thereby compressing and flattening the stack of gloves with a consequent reduction in the height of the stack of gloves. As this process is repeated for each glove that is deposited, the multiple compressions of the growing stack of gloves helps to ensure that the flexible glove material does not rebound to let air creep back into the stack. The final height of the complete stack of gloves is thereby minimized so that the maximum number of interfolded gloves can be provided to the end user within each completed pack. The end result is that it is possible to pack 100 or more disposable interfolded nitrile or latex gloves of standard thickness (rated at 9 Newtons tear strength) inside a card material box having external dimensions of about 130 mm wide by 120 mm deep by 130 mm high. The invention also permits 200 disposable interfolded nitrile or latex gloves of thinner thickness (rated at 6 Newtons tear strength) inside a card material box having external dimensions of about 130 mm wide by 120 mm deep by 165 mm high. The card material may be cardboard, a plastic card material or any other suitable disposable thin sheet material.

The compression of the growing stack of gloves by the piston is also used in an automatic way to control the downward movement of the moveable floor 170. Pressure from the piston 86 causes the floor 170 to move down in a controlled manner during glove stacking such that the topmost stacked glove remains substantially at, or just below, the level of the work surface 164. Because the piston downward movement is fixed, and because the resulting downward movement of the floor is driven purely by the piston pressure, floor moves only as far as is necessary to depending on the height of the glove stack.

The floor may be supported by an upwardly acting spring mechanism 97, with an associated ratchet mechanism permitting only downward movement of the floor under the piston pressure.

After this depositing and compressing stage, the lifting and depositing portion is lifted, as shown in FIG. 15, after which the glove manipulator 138 is withdrawn from the packing station 160 to collect a second glove 106'.

The flaps 171, 173 are then used to fold portions 110 of the second last deposited glove extending beyond the bounds of the recess in towards the recess so that the cuff of this glove is folded over the finger portion of the last glove to be deposited. It should be noted that because the vacuum supply is completely separate from the body of the flaps, there is no need to cut or reduce the vacuum air supply to the perforations 91 in the work surface 164. As soon as the flaps begin to move away from the perforations, the vacuum pressure through the mesh is automatically reduced and then cut so that the gloves are no longer held tightly to the mesh surface of the flaps. Keeping the vacuum supply separate from the flaps is therefore a particularly helpful aspect of the invention and provides several important benefits. First, the weight of each flap 171, 173 is minimized and the construction is simplified as there is no need to provide additional air flow channels to or within the body of the movable flap. Second, because the weight of each flap is minimized, it is easier to move the flap rapidly in either direction, thereby speeding up the packing process and further simplifying the construction of the apparatus. Thirdly, the vacuum airflow is automatically released when the flap 171, 173 moves away from the perforations 91, which avoids the need to switch the vacuum flow on and off or even to provide a positive air flow to the flaps to help dislodge the gloves from the flaps when these have moved fully over the recess. This is a real advantage when gloves are being stacked at a rate of about one glove per second. It is therefore preferred that vacuum pressure applied to the perforation is continuous and constant.

Figure 16:
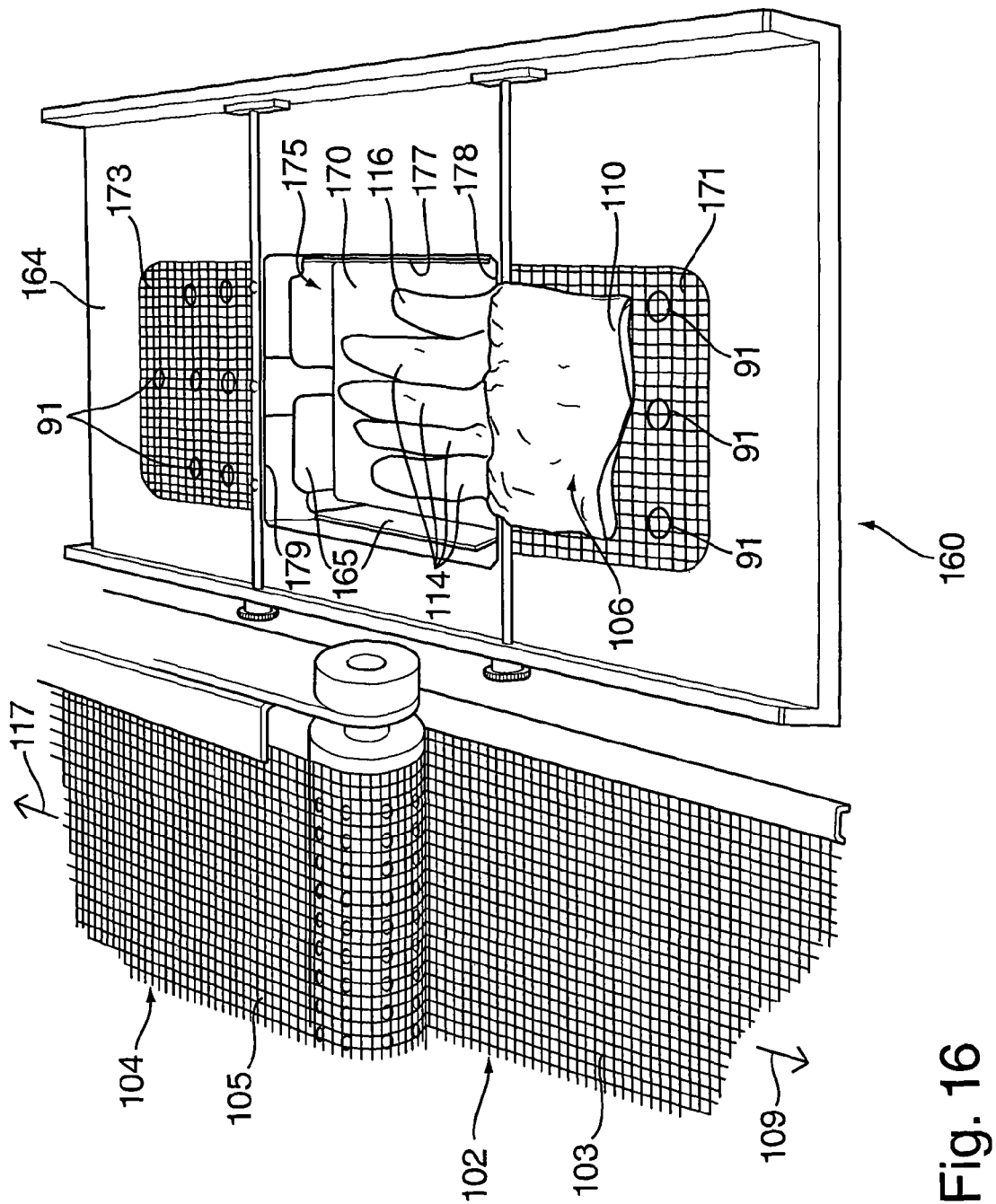
FIG. 16 shows the packing station of FIG. 15 after the glove manipulator has been withdrawn, with a cuff of the deposited glove extending beyond the packing recess and lying over a first movable flap on one side of the packing recess.

FIG. 16 shows the packing station 160 after the glove manipulator 138 has been withdrawn, with a cuff 110 of the deposited glove 106 extending beyond the packing recess and over a first movable flap 171 on one side 178 of the packing recess 175.

Figure 17:
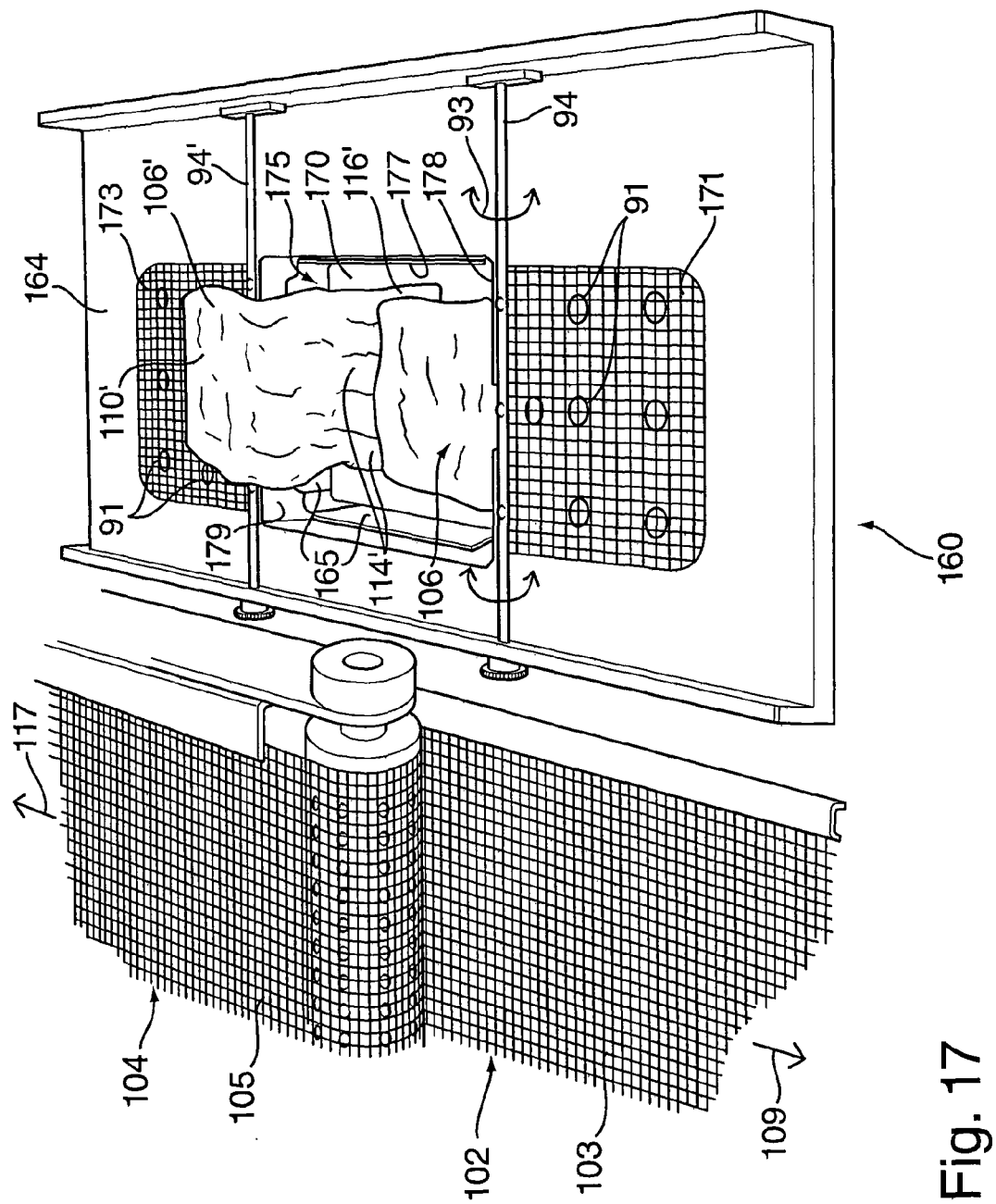
FIG. 17 shows how, after the deposit of a second glove oriented oppositely with respect to the first glove, but with thumbs on the same side of the packing recess, the first movable flap is rotated about a pivot rod to fold the cuff of the first glove over the finger portion of the second glove.

FIG. 17 shows how, after the deposit of a second glove 106' oriented oppositely with respect to the first glove 106, but with thumbs 116, 116' on the same side of the packing recess 175, the first movable flap 171 is rotated 93 about a pivot rod 94 to fold the cuff 110 of the first glove over the finger portion 114', 116' of the second glove 106'. The other flap 173 is mounted on a similar rod 94' and moves in the same way to fold over the cuff 110' of the second glove after a third glove (not shown) has been deposited on the stack in the same orientation as the first glove 106. In this way, an interfolded stack of gloves is built up, with the stack being repeatedly compressed by the piston 86 after the deposit of each glove.

Figure 18:
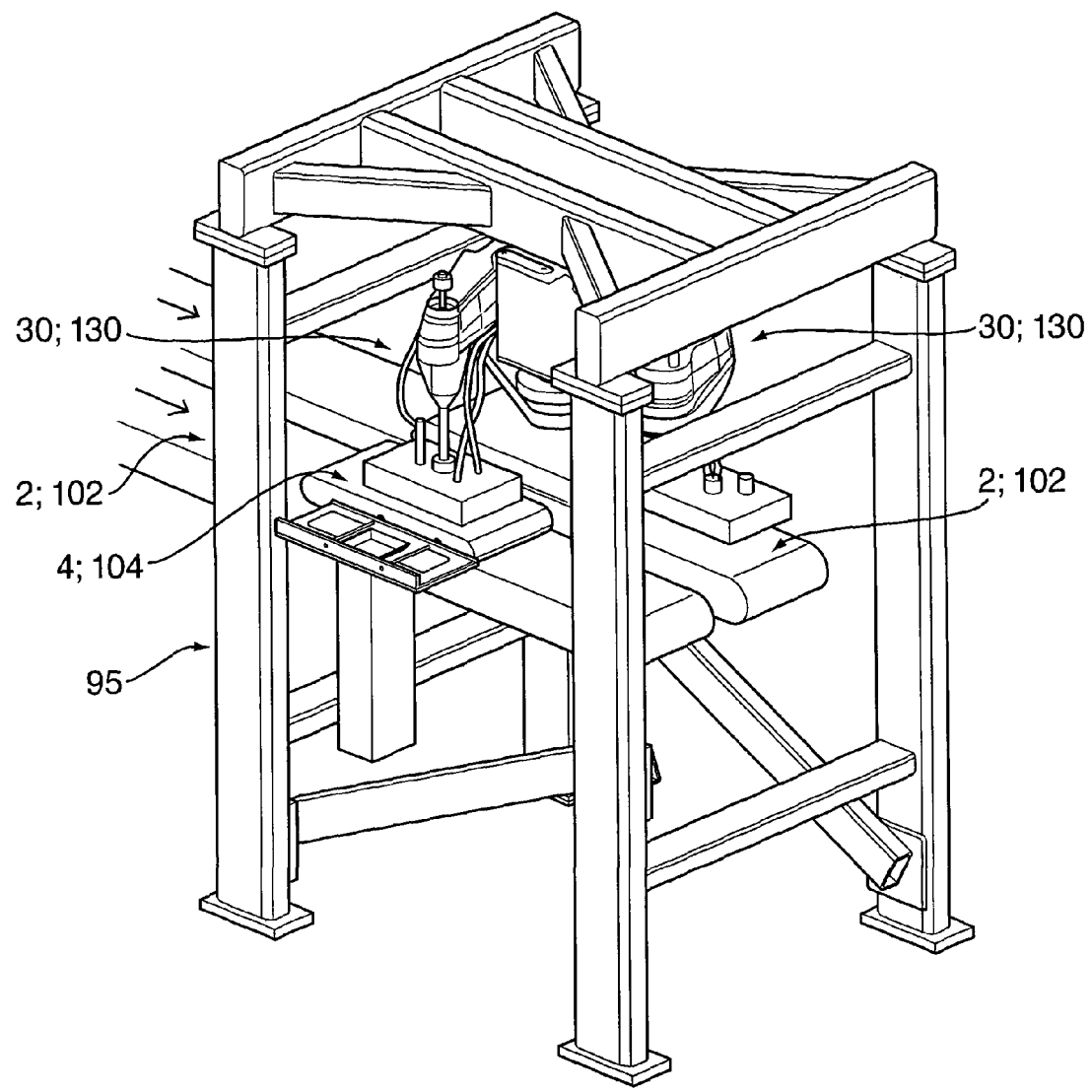
FIG. 18 is perspective view showing how the apparatus for stacking gloves may be paired and how two of the glove placement means may be mounted on a frame from above.
Figure 19:
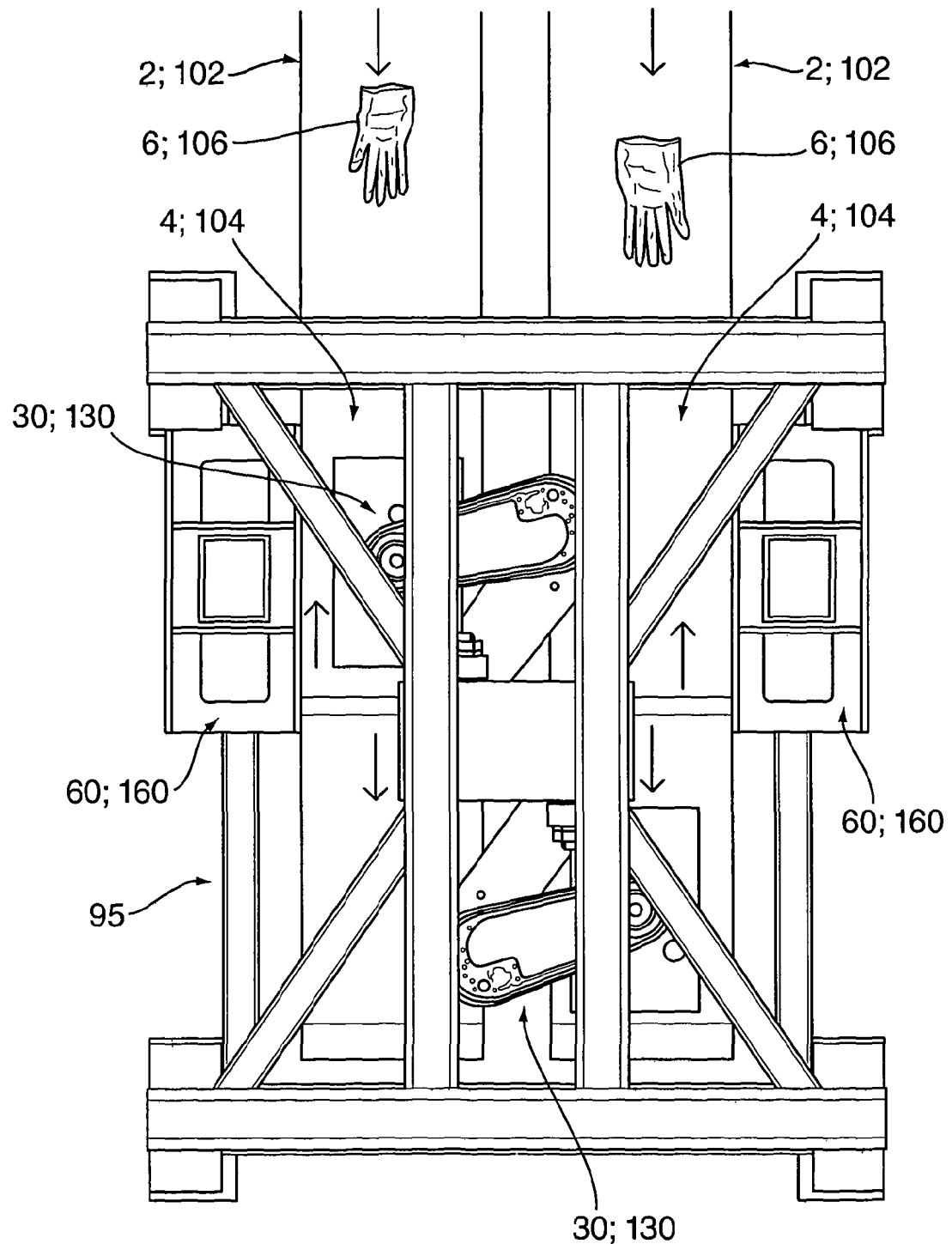
FIG. 19 is a top view of the paired apparatus for stacking gloves of FIG. 18.

FIGS. 18 and 19 show how the various embodiments of the apparatus 1, 101 for stacking gloves described above may be paired into two side-by side production lines and how two of the glove placement means 30, 130 may be mounted on a frame 95 from above. This arrangement is particularly efficient, because a worker at the starting end 19 of the first conveyor 2, 102 may use both hands at the same time to place a glove on each of the first conveyors.

The invention therefore provides a convenient apparatus and method for stacking gloves prior to packing in a dispensing box.

Modification and substitutions by one of ordinary skill in the art are considered to be within the scope of the present invention, which is not to be limited except by the allowed claims and their legal equivalents.

The invention claimed is:

1. A method of folding and stacking gloves using a glove stacking apparatus, said apparatus comprising a packing recess for receiving unfolded gloves to be folded and stacked, a glove manipulator, a movable floor within said recess and a pair of movable flaps adjacent a pair of opposite side edges of said recess, the method comprising the steps of:
    using the glove manipulator to deposit unfolded gloves at said recess for subsequent folding and stacking of said gloves, a portion of each of said deposited gloves initially overlapping alternately one or the other of said opposite side edges of said recess;
    alternately using one or the other of said movable flaps to fold towards said recess said overlapping portion of each of said unfolded glove overlapping said edge to form a stack of folded gloves within said recess;
    lowering said movable floor as required as the stack of folded gloves grows within said recess whereby said stack of folded gloves continues to be retained within said recess as unfolded gloves are added to the stack and folded; and
    repeating the preceding steps to form a stack of folded gloves within the bounds of said recess.

2. A method as claimed in claim 1, in which said folded gloves within the stack of gloves are interfolded for cuff first dispensing from a box dispenser.

3. A method as claimed in claim 2, in which each glove has a cuff portion and a finger portion, and the method comprises the step of using the glove manipulator to deposit said unfolded gloves at said recess with said overlapping portion being the cuff portion of a deposited unfolded glove and with the finger portion of each deposited unfolded glove placed overlying said recess.

4. A method as claimed in claim 3, in which the method comprises the step of using said flaps alternately to fold each of said overlapping cuff portions of an unfolded glove over a finger portion of the previously deposited glove.

5. A method as claimed in claim 1, in which the glove manipulator deposits said unfolded gloves such that a portion of each deposited unfolded glove is contained by said recess and another portion of each deposited unfolded glove overlaps one or the other of said opposite side edges of said recess and lies on one or the other of the movable flaps adjacent said edges.

6. A method as claimed in claim 1, in which the glove stacking apparatus comprises additionally a conveyor having a glove transporting surface, the method comprising the steps of conveying unfolded gloves on said transporting surface presented flat for stacking, and using the glove manipulator to move said conveyed unfolded gloves from said transporting surface prior to depositing said unfolded gloves at said recess.

7. A method as claimed in claim 1, in which the method comprises the step of moving each of said flaps such that said flap extends away from said recess at right angles to a stacking axis of said recess prior to said depositing of said unfolded gloves.

8. A method as claimed in claim 7, in which said recess is inset in a work surface and the method comprises the step of moving each of said flaps to be flat or flush with the work surface prior to said depositing of said unfolded gloves.

9. A method as claimed in claim 1, in which the glove stacking apparatus comprises a source of vacuum pressure that is separate from each of said flaps, each of said flaps having a surface that is permeable to air flow through said surface, and the method comprises the step of using the source of vacuum pressure to apply a vacuum air pressure to said overlapping portion of said unfolded glove from behind said flap and through said permeable surface to pull said overlapping portion of said unfolded glove to said permeable surface prior to folding of said overlapping portion of said unfolded glove towards said recess.

10. A method as claimed in claim 9, in which the application of the vacuum air pressure through said permeable surface is automatically released as said flap moves away from the source of vacuum pressure behind said flap as said flap folds said overlapping portion of said unfolded glove towards said recess.

11. A method as claimed in claim 9, in which said recess is inset in a work surface and the work surface has at least one perforation behind said permeable surface of each flap through which said vacuum air pressure is applied, the method comprising the step of applying said vacuum air pressure to said permeable surface through said at least one perforation, whereby said vacuum air pressure is applied to said overlapping portion of each deposited unfolded glove when each flap is positioned such that said flap extends away from said recess and whereby said vacuum air pressure is automatically released as said flap moves to fold said overlapping portion of said unfolded glove towards said recess.

12. A method as claimed in claim 1, in which each of said flaps is hinged at a pivot adjacent one of said opposite side edges, the method comprising the step of rotating each of said flaps about said pivot as the flap is moved to fold said overlapping portion of said unfolded glove towards said recess.

13. A method of folding and stacking gloves using a glove stacking apparatus, said apparatus comprising a stacking station for forming a stack of folded gloves, at least one conveyor, and a sensing apparatus, the stacking station comprising a packing recess for receiving unfolded gloves to be folded and stacked, a glove manipulator, a movable floor within said recess, a pair of movable flaps adjacent a pair of opposite side edges of said recess, the method comprising the steps of:
  using said conveyor to transport said unfolded gloves to be stacked;
  using said sensing apparatus to sense the presence of said transported unfolded gloves on said conveyor;
  controlling the operation of said glove manipulator in accordance with said sensed presence of said gloves on said conveyor such that the glove manipulator moves said transported unfolded gloves from said glove conveyor and deposits said unfolded gloves at said recess for subsequent folding and stacking of said gloves, a portion of each of said deposited gloves initially overlapping alternately one or the other of said opposite side edges of said recess;
  alternately using one or the other of said movable flaps to fold towards said recess said overlapping portion of each of said deposited gloves to form said stack of folded gloves within said recess; and
  lowering said movable floor as required as the stack of folded gloves grows within said recess whereby said stack of folded gloves continues to be retained within said recess as unfolded gloves are added to the stack and folded.

14. A method of folding and packing a stack of folded gloves into a glove dispensing box using a glove stacking apparatus, said apparatus comprising a packing recess for receiving unfolded gloves to be folded and stacked, a glove manipulator, a movable floor within said recess and a pair of movable flaps adjacent a pair of opposite side edges of said recess, the method comprising the steps of:
  using the glove manipulator to deposit unfolded gloves at said recess for subsequent folding and stacking of said gloves, a portion of each of said deposited gloves initially overlapping alternately one or the other of said opposite side edges of said recess;
  alternately using one or the other of said movable flaps to fold towards said recess said overlapping portion of each of said unfolded gloves overlapping said edge to form a stack of folded gloves within said recess;
  lowering said movable floor as required as the stack of folded gloves grows within said recess whereby said stack of folded gloves continues to be retained within said recess as unfolded gloves are added to the stack and folded;
  repeating the preceding steps to form a stack of folded gloves within the bounds of said recess, and after said stack of folded gloves has been formed then packing said stack of folded gloves in said glove dispensing box by placing an open mouth of the box over said recess and then moving the floor to press the stacked and folded gloves out of said recess and into the open box; and
  closing and sealing the open mouth of the box.

15. A method of folding and stacking gloves using a glove stacking apparatus, said apparatus comprising a packing recess for receiving unfolded gloves to be folded and stacked, a glove manipulator, a movable floor within said recess, a first movable flap and a second movable flap, said recess having a first side edge and a second side edge, said edges being opposite side edges of said recess and the first movable flap being adjacent the first side edge and the second movable flap being adjacent the second side edge, the method comprising the steps of:
  i) using the glove manipulator to deposit a first unfolded glove proximate said recess, such that a first portion of said first unfolded glove is deposited to overlie said recess and a second portion of said first glove is deposited overlapping the first side edge of said recess;
  ii) subsequent to using the glove manipulator to deposit said first unfolded glove proximate said recess, using the glove manipulator to deposit a second unfolded glove proximate said recess, such that a first portion of said second unfolded glove is deposited on top of said first portion of said first glove overlying said recess, and such that a second portion of said second glove is deposited overlapping the second side edge of said recess opposite said first side edge of said recess;
  iii) subsequent to using the glove manipulator to deposit said second unfolded glove proximate said recess, using the first flap to fold said second portion of said first glove deposited overlapping the first side edge of said recess towards said recess so that said second portion of said first glove overlies said first portion of said second glove in said recess;
  iv) subsequent to using the first flap to fold said second portion of said first glove deposited overlapping the first side edge of said recess towards said recess, using the glove manipulator to deposit a third unfolded glove proximate said recess, such that a first portion of said third unfolded glove is deposited on top of said second portion of said first glove overlying said recess and such that a second portion of said third glove is deposited overlapping the first side edge of said recess opposite said second side edge of said recess;
  v) subsequent to using the glove manipulator to deposit said third unfolded glove proximate said recess, using the second flap to fold said second portion of said second glove deposited overlapping the second side edge of said recess towards said recess so that said second of portion of said second glove overlies said first portion of said third glove overlying said recess; and
  vi) repeating steps ii) to v) with subsequent gloves while lowering said movable floor to form a stack of interfolded gloves within said recess.

* * * * *